US009765282B2

(12) United States Patent
Berthier et al.

(10) Patent No.: US 9,765,282 B2
(45) Date of Patent: Sep. 19, 2017

(54) POLYSILOXANE CONJUGATES AS FRAGRANCE DELIVERY SYSTEMS

(71) Applicant: FIRMENICH SA, Geneva (CH)

(72) Inventors: Damien Berthier, Geneva (CH); Yongtao Wu, Shanghai (CN); Andreas Herrmann, Geneva (CH); Arnaud Struillou, Geneva (CH); Estelle Rassat, Geneva (CH); Nicolas Paret, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/900,157

(22) PCT Filed: Jun. 17, 2014

(86) PCT No.: PCT/EP2014/062699
§ 371 (c)(1),
(2) Date: Dec. 19, 2015

(87) PCT Pub. No.: WO2014/202591
PCT Pub. Date: Dec. 24, 2014

(65) Prior Publication Data
US 2016/0145534 A1 May 26, 2016

(30) Foreign Application Priority Data

Jun. 19, 2013 (EP) .................................. 13172782

(51) Int. Cl.
| | | |
|---|---|---|
| *A61Q 5/02* | (2006.01) | |
| *C11B 9/00* | (2006.01) | |
| *C08G 77/392* | (2006.01) | |
| *C11D 3/50* | (2006.01) | |
| *A61K 8/35* | (2006.01) | |
| *A61Q 13/00* | (2006.01) | |
| *A61K 8/899* | (2006.01) | |
| *D06M 13/00* | (2006.01) | |
| *C08G 77/38* | (2006.01) | |
| *D06M 15/643* | (2006.01) | |
| *D06M 23/02* | (2006.01) | |
| *C08G 77/28* | (2006.01) | |
| *A61Q 5/12* | (2006.01) | |

(52) U.S. Cl.
CPC .............. *C11B 9/0034* (2013.01); *A61K 8/35* (2013.01); *A61K 8/899* (2013.01); *A61Q 13/00* (2013.01); *C08G 77/38* (2013.01); *C08G 77/392* (2013.01); *C11B 9/0003* (2013.01); *C11B 9/0015* (2013.01); *C11B 9/0042* (2013.01); *C11B 9/0046* (2013.01); *C11B 9/0053* (2013.01); *C11B 9/0057* (2013.01); *C11D 3/502* (2013.01); *C11D 3/507* (2013.01); *D06M 13/005* (2013.01); *D06M 15/643* (2013.01); *D06M 23/02* (2013.01); *A61K 2800/57* (2013.01); *A61Q 5/02* (2013.01); *A61Q 5/12* (2013.01); *C08G 77/28* (2013.01)

(58) Field of Classification Search
None
See application file for complete search history.

(56) References Cited

U.S. PATENT DOCUMENTS

| | | | |
|---|---|---|---|
| 4,137,180 A | 1/1979 | Naik et al. | |
| 5,236,615 A | 8/1993 | Trinh et al. | |
| 7,723,286 B2 * | 5/2010 | Fehr ....................... | C11D 3/507 510/101 |
| 2010/0035790 A1 | 2/2010 | Lange et al. | |
| 2010/0120657 A1 | 5/2010 | Lange et al. | |

FOREIGN PATENT DOCUMENTS

| | | | |
|---|---|---|---|
| EP | 799885 A1 | 10/1997 | |
| WO | WO9734986 A1 | 9/1997 | |
| WO | WO 99/46318 * | 9/1999 | ........... C08G 77/388 |
| WO | WO03049666 A2 | 6/2003 | |
| WO | WO2005041908 A1 | 5/2005 | |
| WO | WO2008044178 A1 | 4/2008 | |
| WO | WO2012113746 A1 | 8/2012 | |

OTHER PUBLICATIONS

Andreas Herrmann "Controlled Release of Volatiles under Mild Reaction Conditions: From Nature to Everyday Products" Angew. Chem. Int. Ed 2007, 46, 5836-5863.*
Berthier et al. "Influence of the Backbone Structure on the Release of Bioactive Volatiles from Maleic Acid-Based Polymer Conjugates" Bioconjugate Chem. 2010, 21, 2000-2012.*
International Search Report and Written Opinion, application PCT/EP2014/062699, mailed Jul. 4, 2014.

* cited by examiner

*Primary Examiner* — Robert S Loewe
(74) *Attorney, Agent, or Firm* — Winston & Strawn LLP

(57) ABSTRACT

The present invention relates to the field of perfumery. More particularly, it concerns polymers derived from siloxane derivatives and comprising at least one β-thio carbonyl moiety capable of liberating an active molecule such as, for example, an α,β-unsaturated ketone or aldehyde. The present invention concerns also the use of polymers in perfumery as part of a perfuming or malodor counteracting composition as well as the perfuming compositions or perfumed articles comprising the invention's compounds.

20 Claims, No Drawings

POLYSILOXANE CONJUGATES AS FRAGRANCE DELIVERY SYSTEMS

TECHNICAL FIELD

This invention relates to polysiloxane conjugates in the field of perfumery. More particularly, it concerns polymers derived from siloxane derivatives and comprising at least one β-thio carbonyl moiety capable of liberating an active molecule such as, for example, an α,β-unsaturated ketone or aldehyde. The present invention concerns also the use of polymers or co-polymers in perfumery as part of a perfuming or malodor counteracting composition, as well as the perfuming compositions or perfumed articles comprising the invention's compounds.

PRIOR ART

The perfume industry has a particular interest for derivatives which are capable of prolonging the effect of active ingredients over a certain period of time, for example in order to overcome the problems encountered when using perfuming ingredients which are too volatile or have a poor substantivity. In particular, the industry is interested in derivatives capable of providing an improved olfactive performance. Said improvement can be in time, in intensity or in the effective amount of active compound released.

The patent application WO 03/049666 describes a class of compounds capable of prolonging the effect of active ingredients. Among these compounds there are mentioned polymers, citing as specific examples a few styrene co-polymers. However, although the performance described in the examples for several monomeric derivatives is quite good, the performance of the polymers is relatively modest (see Examples 6 and 7 of the application). There is therefore still a need to improve the release properties of polymer-based ingredients capable of prolonging the effect of active ingredients.

In the patent application WO 2005/041908, nano-sized delivery systems consisting of an inorganic particle covalently bound to at least one organic pro-perfume or pro-drug moiety are disclosed. The systems of the invention are able to deliver perfuming or pharmaceutical active ingredients. Other aspects of the present invention, for instance, are the use of said systems in perfumery, as well as the perfuming compositions or perfumed articles comprising the invention's delivery systems. Silica particles are disclosed but their performance is not satisfactory.

The patent application WO 2008/044178 deals with co-polymers, derived from a maleic anhydride derivative and an ethylenic derivative, comprising at least one β-thio carbonyl moiety capable of liberating an active molecule such as, for example, an α,β-unsaturated ketone, aldehyde or carboxylic ester. These polymers are quite different from the present ones.

The two documents US 2010/0120657 and US 2010/0035790 disclose non-flowable crosslinked siloxane-based polymers aimed to react with the target surface to improve deposition and fragrance delivery. Such non-flowable polymers are clearly the most suitable solution indicated by the prior art documents, but we found that it was possible to achieve only poor dispersion and therefore only poor deposition and poor delivery. Notwithstanding that the prior art clearly teaches the need to promote the chemical binding of the polymers to the surface, this is clearly not the best solution on the long term, because chemical binding will modify the target surface.

The aim of the present invention is to provide alternative polymeric materials capable to perform better than the standard free oil and possibly as good as or even better than known commercial monomeric profragrances, while maintaining good flowable properties. The aimed target of the present invention, even if met partially, is known by the person skilled in the art to be difficult to be achieved for polymeric profragrances.

The invention's co-polymers are believed to have never been specifically disclosed or suggested in the prior art, nor their particular performances in the field of perfume release.

DESCRIPTION OF THE INVENTION

We have now surprisingly discovered the existence of particular polymers derived from siloxane derivatives and comprising at least one β-thio carbonyl moiety capable of liberating an active molecule, namely an enone, and having a superior performance when compared with the free active molecule and an as good as, or even superior performance when compared with prior art polymers. As "active molecule" we mean here any molecule capable of bringing an odor benefit or effect into its surrounding environment, and in particular an odoriferous molecule, i.e. a perfuming ingredient, such as an α,β-unsaturated ketone or aldehyde.

It is understood that in the present invention the term "polymers" includes homo-polymers, i.e. obtained by the polymerization of one type of monomers (without considering the terminal groups), as well as co-polymers, i.e. obtained by the polymerization of two or more types of monomers. It is understood that in the present invention the term "polymers" includes also oligomers (such as trimers, tetramers or higher oligomers).

The present invention's polymers can be used as perfuming or malodor counteracting ingredients.

A first object of the present invention concerns a polymer, capable of releasing in a controlled manner an odoriferous α,β-unsaturated ketone or aldehyde, and comprising at least one repeating unit of formula

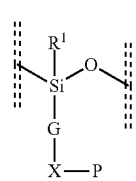

(I)

wherein the double hatched lines indicate the bonding to another repeating unit and
$R^1$ represents a $C_1$ to $C_{16}$ hydrocarbon group;
P represents a group susceptible of generating an odoriferous α,β-unsaturated ketone or aldehyde and is represented by formula

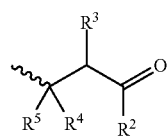

(II)

in which the wavy line indicates the location of the bond between said P and X;

$R^2$ represents a hydrogen atom, a $C_1$ to $C_{15}$ linear, cyclic or branched alkyl, alkenyl or alkadienyl radical, optionally substituted by one to four $C_1$ to $C_4$ alkyl groups; and $R^3$, $R^4$ and $R^5$, independently of each other, represent a hydrogen atom, a $C_6$ to $C_{10}$ aromatic ring or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bound together to form a saturated or unsaturated ring having 5 to 20 carbon atoms and, including the carbon atom to which said $R^2$, $R^3$, $R^4$ or $R^5$ groups are bound, this ring being optionally substituted by one or two $C_1$ to $C_8$ linear, branched or cyclic alkyl or alkenyl groups;

X represents a sulfur atom;

G represents a $C_2$-$C_8$ hydrocarbon group optionally comprising 1 or 2 oxygen, sulfur and/or nitrogen atoms.

It is understood that by " . . . hydrocarbon group . . . " it is meant that said group is consisting of hydrogen and carbon atoms and can be in the form of a linear, branched or cyclic, aromatic, alkyl, alkenyl, or alkynyl group, e.g., a linear alkyl group, or can also be in the form of a mixture of said types of groups, e.g. a specific group may comprise a linear alkyl, a branched alkenyl (e.g. having one or more carbon-carbon double bonds), a (poly)cyclic alkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is meant also a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

As "odoriferous α,β-unsaturated ketone or aldehyde", expression used in the definition of P, we mean here an α,β-unsaturated ketone or aldehyde which is recognized by a person skilled in the art as being used in perfumery as perfuming ingredient. By "perfuming ingredient" it is meant here a compound, which is used in a perfuming preparation or a composition to impart a hedonic effect. In other words such perfuming ingredient, to be considered as being a perfuming one, must be recognized by a person skilled in the art as being able to impart or modify in a positive or pleasant way the odor of a composition, and not just as having an odor.

In general, said odoriferous α,β-unsaturated ketone or aldehyde is a compound having from 8 to 20 carbon atoms, or even more, preferably between 10 and 15 carbon atoms.

According to any embodiment of the invention, P may represent a group of the formulae (P-1) to (P-13), in the form of any one of its isomers:

(P-1)

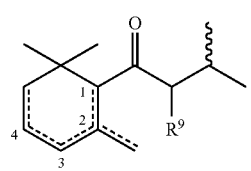

(P-2)

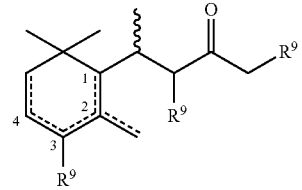

(P-3)

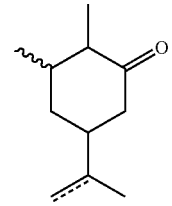

(P-4)

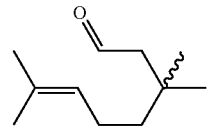

(P-5)

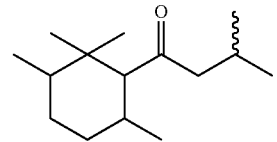

(P-6)

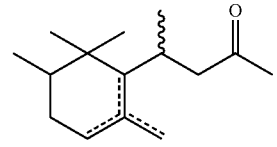

(P-7)

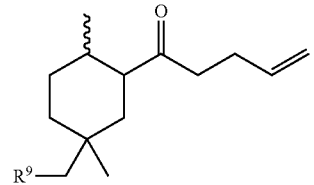

(P-8)

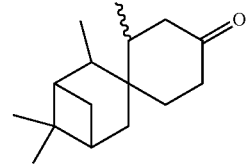

(P-9)

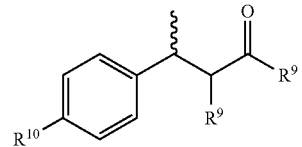

(P-10)

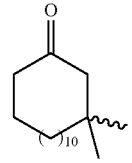

-continued (P-11)
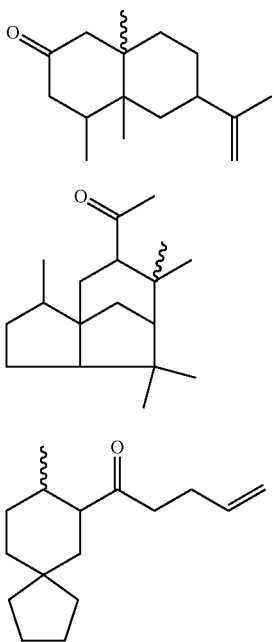

(P-12)

(P-13)
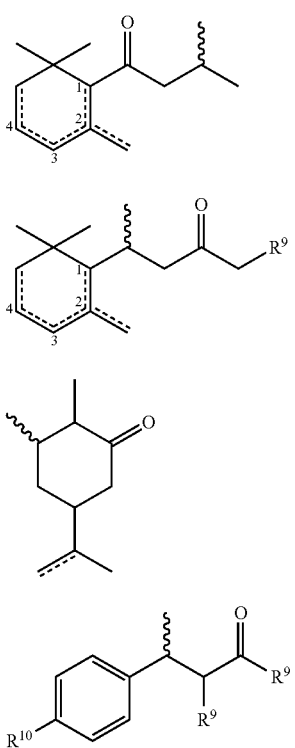

in which formulae the wavy lines have the meaning indicated above and the dotted lines represent a single or double bond, $R^9$ being a hydrogen atom or a methyl group and $R^{10}$ representing a hydrogen atom, a hydroxy or methoxy group or a $C_1$-$C_4$ linear or branched alkyl group.

According to any embodiment of the invention, P may represent a radical of the formula (P-1)'

(P-2)'

(P-3)

(P-9)

-continued (P-5)

(P-6)

(P-7)

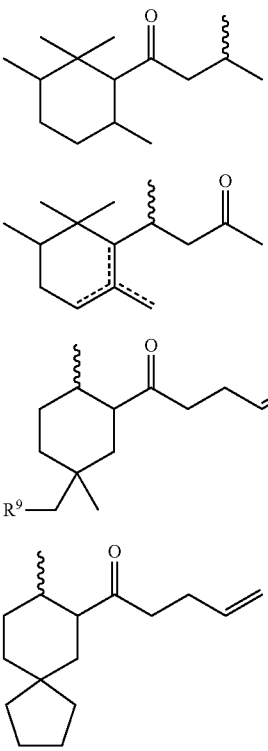

(P-13)

wherein wavy lines, dotted lines, $R^9$ and $R^{10}$ have the meaning indicated above.

According to any embodiment of the invention, P may represent a radical of the formula (P-1), (P-2), (P-1)', (P-2)', (P-3), (P-7) or (P-13) as defined above. Even more particularly P may represent a compound of formula (P-1), (P-7) or (P-13).

According to any embodiment of the invention, G may represent a $C_2$-$C_5$ hydrocarbon group. According to any embodiment of the invention, G may represent a $C_2$-$C_5$ alkanediyl group, such as a $C_2$, $C_3$ or $C_4$ linear or branched alkanediyl groups.

According to any embodiment of the invention, $R^1$ represents a $C_1$ to $C_{10}$ linear, cyclic or branched alkyl, alkenyl or alkadienyl radical, optionally substituted by one or two $C_{1-4}$ alkyl groups or a $C_{6-12}$ aromatic ring.

According to any embodiment of the invention, said $R^1$ represents a $C_1$ to $C_4$ linear or branched alkyl group. In particular $R^1$ may represent a methyl group.

According to any embodiment of the invention, the invention's polymer may be characterized by a weight average molecular weight ($M_w$) comprised in the range between 370 Da and 50000 Da, particularly between 500 Da and 20000 or 30000 Da, particularly between 1000 Da and 10000 Da, more particularly between 1500 Da and 5000 Da or even 4500 Da.

According to any embodiment of the invention, the invention's polymers may be characterized by a viscosity (V) comprised in the range between 0.3 (Pa·s) and 100 (Pa·s), particularly between 0.5 (Pa·s) and 60 (Pa·s), more particularly between 1.0 (Pa·s) and 20 or 30 (Pa·s).

In particular one may mention the combination of any one of the above weight average molecular weight ($M_w$) ranges with any one of the above viscosity (V) ranges.

According to any embodiment of the invention, the invention's polymers may be characterized by a combination of $M_w$ and V ranges, such as that the polymers can also be characterized by a ratio $[1000*V/M_w]$ comprised in the range between 0.3 (Pa·s)/Da and 10 (Pa·s)/Da, or comprised in the range between 0.3 (Pa·s)/Da and 6 (Pa·s)/Da.

According to any embodiment of the invention, the polymers can be co-polymers of the repeating unit (I) and other repeating units. Said co-polymers may be in the form of a random co-polymer or of a block co-polymer. According to any embodiment of the invention, the co-polymer is preferentially of the random, or statistic, type.

According to any embodiment of the invention, said polymer is a homo-polymer or alternatively it is a co-polymer.

According to any embodiment of the invention, the co-polymer comprises repeating units (I), and siloxane repeating units other that unit (I). In particular said co-polymer may comprise essentially (i.e. more than 90%, 95% or even 100% molar percent) siloxane repeating units. Polymers comprising 100% molar percent of siloxane repeating units are preferred.

Furthermore, it is also useful to mention that in said invention's co-polymers the total amount of the repeating unit (I), relative to the total amount of repeating units and without accounting the terminal groups, (hereinafter (I)/(Tot) and expressed in molar percent) can be comprised between 5% and 100%, and in particular between 30% and 100%, or even between 45% and 95% or 100%.

As mentioned above, the invention's co-polymers may comprise at least one other repeating unit, preferably another siloxane. According to any embodiment of the invention, said other repeating units can be of the formulae (III) or (IV)

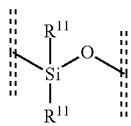
(III)

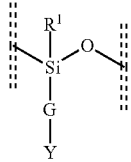
(IV)

wherein the double hatched lines, G and $R^1$ have the same meaning as described for formula (I);
each $R^{11}$ group represents independently of each other a $C_6$ to $C_{12}$ aromatic ring or a $C_1$ to $C_{18}$ linear, cyclic or branched alkyl group, or a $C_1$ to $C_6$ linear, cyclic or branched alkyloxy group; and
Y represents a group of formulae a) to g)

a)
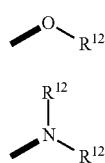

b)
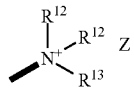

c)
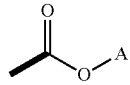

d)
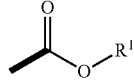

e)

f)

g)

with A being a hydrogen atom or an alkali metal atom, $R^{12}$ being a $C_1$ to $C_{18}$ linear or branched alkyl group, $R^{13}$ being a hydrogen atom or a $R^{12}$ group and Z being a monoanion.

According to any embodiment of the invention, by "$C_6$ to $C_{12}$ aromatic group or ring" it is meant a phenyl or naphthyl group, optionally substituted with other groups (such as alkyl groups) allowing to obtain the desired number of carbon atoms.

According to any embodiment of the invention, each of said $R^{11}$ group represents, independently of each other, a phenyl group or a $C_1$ to $C_3$ linear or branched alkyl group, or a $C_{16}$ to $C_{18}$ linear alkyl group. According to any embodiment of the invention, at least one of said $R^{11}$ groups is a methyl group. According to any embodiment of the invention, each $R^{11}$ group is a methyl group or alternatively one is a methyl group and the other is a $C_{16}$ to $C_{18}$ linear alkyl group.

According to any embodiment of the invention, said Y represents a group of formula b), c), d), e), f) or g) and in particular a group of formula d), f) or g).

According to any embodiment of the invention, said $R^{12}$ represents a $C_1$ to $C_3$ linear or branched alkyl group, or a $C_{16}$ to $C_{18}$ linear alkyl group. According to any embodiment of the invention, at least one or two of said $R^{12}$ groups is a methyl group or each $R^{12}$ groups is a methyl group.

According to any embodiment of the invention, said Z represents a halide, such as $Br^-$ or $Cl^-$, or a sulfate, such as $CH_3SO_4^-$ or $ASO_4^-$ with A being defined as above, or a $C_{1-6}$ carboxylate.

According to any embodiment of the invention, the co-polymer of the invention can also be characterized by a molar ratio of the repeating units (I)/[(III)+(IV)] comprised between 99/1 and 20/80, or comprised between 90/10 and 40/60, or even between 85/15 and 45/55.

According to any embodiment of the invention, the polymer of the invention can also be characterized by being not cross-linked, and in particular by the siloxane skeleton not being cross-linked. According to any embodiment of the invention, said invention's polymer can be characterized by comprising, in addition to the units (I), only siloxane units of the (M) or (D) type, and not having (T) or (Q) type siloxane units. For the sake of clarity, by the expression "(M), (D), (T) or (Q) type siloxane units" it is meant the usual meaning of the art, i.e. units of formula:

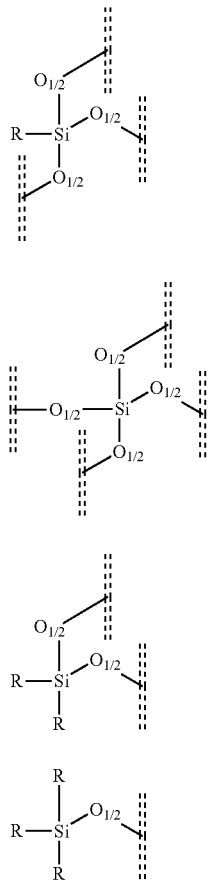

(T)

(D)

(M)

wherein, in the present context, said (D) and (M) units represent groups of formula (III), (IV) and (V) as defined in the description;

so that a poly-siloxane based only on units (I), as well as of (D) and (M) units is basically a linear polymer.

In particular according to any embodiment of the invention, said polymer is linear and comprises only siloxane units of (III), (IV) and (V) types, and of formula (I).

According to any embodiment of the invention, a particular type of polymers of the invention are the ones obtainable by a process comprising the following steps:

I) reacting together, at a temperature comprised between 20° C. and 95° C., preferably between 60° C. and 95° C.:
   a monomer of formula (i)

wherein $R^1$, G, P and X have the same meaning as in formula (I) and $R^{12}$ represents a $C_{1-3}$ alkyl group, in particular a methyl or ethyl group;

optionally monomers of formulae (ii) and/or (iii)

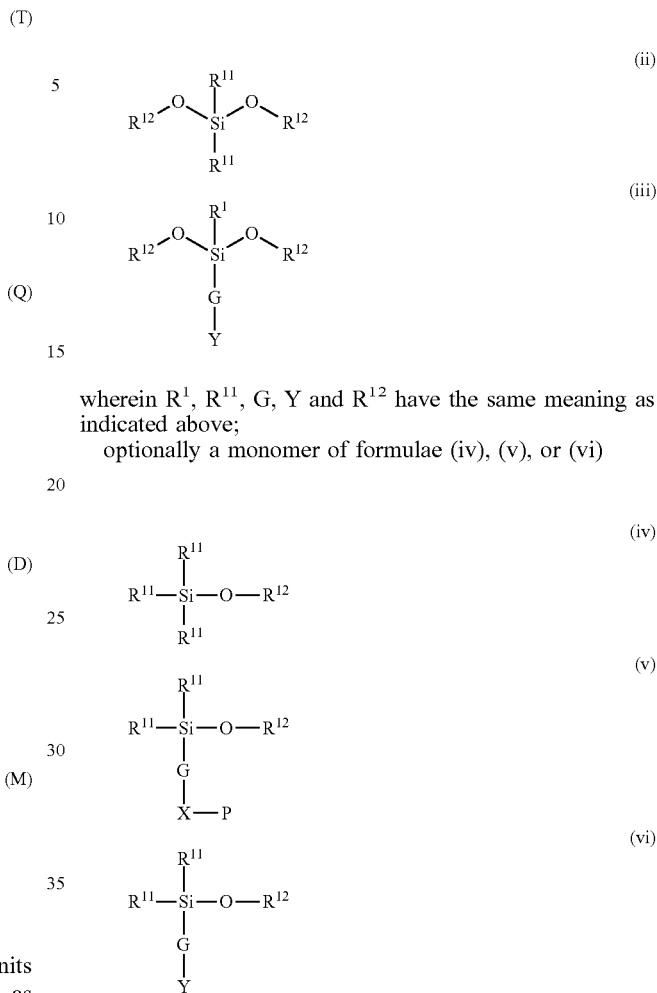

wherein $R^1$, $R^{11}$, G, Y and $R^{12}$ have the same meaning as indicated above;

optionally a monomer of formulae (iv), (v), or (vi)

wherein $R^{11}$, $R^{12}$, G, X, P and Y have the same meaning as indicated above;
   and between 0.5 and 1.1 equimolar amounts of water with respect to the O—$R^{12}$ groups; and
   optionally, but preferably, an amount of a base;

II) optionally, evaporating the alcohol $R^{12}$—OH obtained after polymerization.

According to any embodiment of the invention, alternatively, and in particular in the case that X is a sulfur atom, a particular type of polymers of the invention are the ones obtainable by a process comprising the following steps:

I) reacting together, at a temperature comprised between 20° C. and 95° C., preferably between 60° C. and 95° C.:
   a monomer of formula

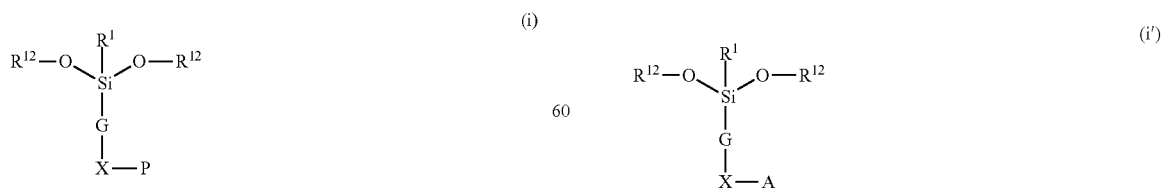

wherein $R^1$, G, $R^{12}$ and X have the same meaning as indicated above and A represents a hydrogen atom or alkali metal atom;

optionally monomers of formulae (ii) and/or (iii)

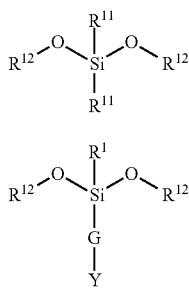

(ii)

(iii)

wherein $R^1$, $R^{11}$, $R^{12}$, G and Y have the same meaning as indicated above;
optionally a monomer of formulae (iv), (v), or (vi)

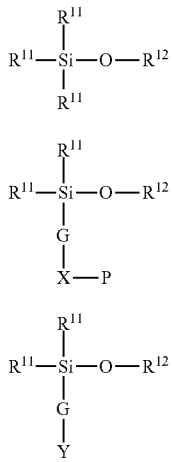

(iv)

(v)

(vi)

wherein $R^{11}$, $R^{12}$, G, X, P and Y have the same meaning as indicated above;
and between 0.5 and 1.1 equimolar amounts of water with respect to the O—$R^{12}$ groups; and
optionally, but preferably, an amount of a base;
II) reacting the polymers obtained in the previous step with an odoriferous compound of formula

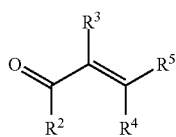

(P')

wherein the configuration of the carbon-carbon double bond can be of the (E) or (Z) type and the symbols $R^2$, $R^3$, $R^4$ and $R^5$ have the meaning indicated in formula (II), and under conditions allowing the formation of the repeating unit (I); and
III) optionally, after step I) or II), evaporating the alcohol $R^{12}$—OH obtained after polymerization.

According to any embodiment of the invention, the amount of water used in the above process can be comprised between 0.7 and 1.0 equimolar amounts of water with respect to the O—$R^{12}$ groups.

For the sake of clarity, by the expression "an amount of a base" or the similar, it is here meant that the reaction is performed in a basic pH, in general comprised above 10, or 12 or even 14, and that the base can be any base and in particular a hydroxide such as NaOH or KOH or triethanolamine.

The monomers of formulae (iv), (v), and (vi) are meant to be end-chain units.

According to any embodiment of the invention, said polymer has terminal groups, which can be of various nature, depending on the manner of the preparation of the polymer. In particular said terminal groups are siloxane groups of type (M) of formula:

$$—O—Si(OR^{13})_a(G\text{-}B)_b(R^{14})_c \qquad (V)$$

wherein each a, b and c is either 0, 1, 2 or 3 and (a+b+c)=3, and in particular b can be 0;
G represents a group as defined herein above;
each B represents independently from each other a X—P or a Y group, as defined above;
each $R^{13}$ represents independently from each other a hydrogen atom or a $R^{12}$ group as defined above; and
each $R^{14}$ represents independently from each other a $R^1$ or a $R^{11}$ group as defined above.

According to any embodiment of the invention, said terminal group is a $Si(OH)_3$, $Si(OR^{12})_3$ or $Si(R^{11})_3$ group. In particular said terminal group is a $Si(OH)_3$, $Si(OR^{12})_3$ or $Si(Me)_3$ group.

Said monomer (i) can be obtained by [1,4]-addition of an appropriate compound of formula (i') (wherein A represents a hydrogen atom or an alkali metal atom) to an odoriferous α,β-unsaturated ketone or aldehyde of formula (P').

The other monomers are either commercially available or can be obtained following standard procedures well known by a person skilled in the art.

According to any embodiment of the invention, the polymer of the invention is a linear co-polymer wherein the molar ratio of the repeating units (I)/[(III)+(IV)] is comprised between 85/15 and 45/55, and in formula (I) P is defined hereinabove (in particular as defined in formulae (P-1) to (P-13);
X represents a sulfur atom;
$R^1$ is a methyl group;
G represents a linear $C_3$-$C_5$ alkanediyl group; and
said polymer having
a weight average molecular weight ($M_w$) comprised in the range between 1000 Da and 5000 Da;
terminal groups of formula:

$$—O—Si(OR^{13})_a(R^{14})_c \qquad (V')$$

wherein each a and c is either 0, 1, 2 or 3 and (a+c)=3;
each $R^{13}$ represents independently from each other a hydrogen atom or a $R^{12}$ group as defined above; and
each $R^{14}$ represents independently from each other a $R^1$ or a $R^{11}$ group as defined above;
and optionally a viscosity (V) comprised in the range between 1.0 (Pa·s) and 60 (Pa·s).

Owing to their particular chemical structure the invention's polymers are capable of releasing, via a decomposition reaction, a residue and an odoriferous molecule such as, for example, an α,β-unsaturated ketone or aldehyde of formula (P').

It is not possible to provide an exhaustive list of compounds of formula (P'), which can be used in the synthesis of the compound (I) and subsequently be released. However, the following can be named as preferred examples: alpha-damascone, beta-damascone, gamma-damascone, deltadamascone, alpha-ionone, beta-ionone, gamma-ionone, delta-ionone, beta-damascenone, 3-methyl-5-propyl-2-cyclohexen-1-one, 1-(3,3- or 5,5-dimethyl-1-cyclohexen-1-yl)-4-penten-1-one (Neobutenone®, origin: FirmenichSA), 1-(3-ethyl-3-methyl-1-cyclohexen-1-yl)-4-penten-1-one, 1-(5-ethyl-5-methyl-1-cyclohexen-1-yl)-4-penten-1-one, 1-(spiro[4.5]dec-6- or 7-en-7-yl)pent-4-en-1- one, 2-methyl-5-(prop-1-en-2-yl)cyclohex-2-enone (carvone), 8- or 10-methyl-alpha-ionone, 2-octenal, 1-(2,2,3,6-tetramethyl-1-cyclohexyl)-2-buten-1-one, 4-(2,2,3,6-tetramethyl-1-cyclohexyl)-3-buten-2-one, 2-cyclopentadecen-1-one, 4,4a-dimethyl-6-(prop-1-en-2-yl)-4,4a,5,6,7,8-hexahydronaphthalen-2(3H)-one (nootkatone), cinnamaldehyde, 2,6,6-trimethyl-bicyclo[3.1.1]heptane-3-spiro-2'-cyclohexen-4'-one and 3,7-dimethylocta-2,6-dienal (citral).

According to a particular embodiment of the invention the following compounds of formula (P') can be cited: the damascones, ionones, beta-damascenone, 1-(3,3- or 5,5-dimethyl-1-cyclohexen-1-yl)-4-penten-1-one, 1-(5-ethyl-5-methyl-1-cyclohexen-1-yl)-4-penten-1-one, carvone, 1-(2,2,3,6-tetramethyl-1-cyclohexyl)-2-buten-1-one, 4-(2,2,3,6-tetramethyl-1-cyclohexyl)-3-buten-2-one and citral.

Therefore, the invention's compounds capable of releasing such compounds (P'), or carrying the corresponding P group, are also a particularly appreciated embodiment of the invention.

An example of the above-mentioned decomposition reaction is illustrated in the following scheme, wherein only one repeating unit is shown:

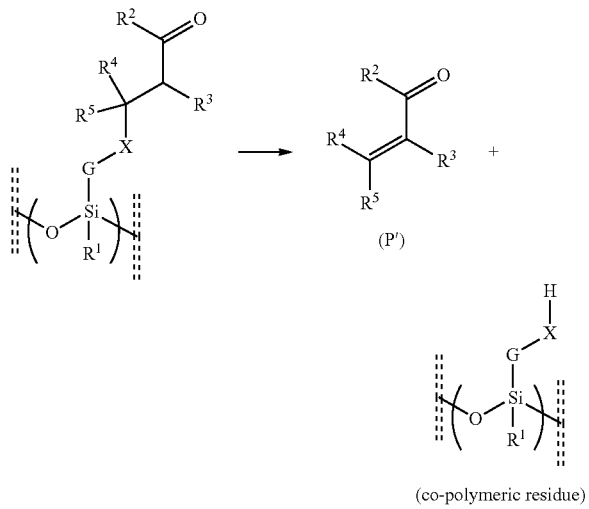

(co-polymeric residue)

and the decomposition reaction, which leads to the release of the odoriferous molecules, is believed to be influenced by the presence of oxygen, pH changes or by heat, but may also be triggered by other types of mechanisms.

As mentioned above, the invention concerns the use of the above-described co-polymers as perfuming ingredients. In other words it concerns a method to confer, enhance, improve or modify the odor properties of a perfuming composition or of a perfumed article, which method comprises adding to said composition or article an effective amount of at least a polymer according to the invention. By "use of an invention's polymer" it has to be understood here also the use of any composition containing said polymer and which can be advantageously employed in perfuming industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's polymer as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

Generally speaking, by "perfumery base" we mean here a composition comprising at least one perfuming co-ingredient.

Said perfuming co-ingredient is not a co-polymer according to the invention. Moreover, by "perfuming co-ingredient" it is meant here a compound, which is used in a perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Other suitable co-ingredients optionally used in combination with the polymers according to the present invention comprise tertiary amines, in particular those with high water solubility, such as triethanolamine, methyldiethanolamine, dimethylethanolamine, alkyldiethanolamines and ethoxylated alkyldiethanolamines.

An invention's composition consisting of at least one co-polymer and at least one perfumery carrier represents a particular embodiment of the invention as well as a perfuming composition comprising at least one polymer, at least one perfumery carrier, at least one perfumery base, and optionally at least one perfumery adjuvant.

It is useful to mention here that the possibility to have, in the compositions mentioned above, more than one of the invention's polymers is important as it enables the perfumer to prepare accords, perfumes, possessing the odor tonality of various compounds of the invention, creating thus new tools for their work. The invention's polymer may also be used in the presence of other perfume delivery systems, such as capsules or profragrances.

Furthermore, an invention's polymer, or a perfuming composition comprising it, is a useful perfuming ingredient, which can be advantageously used in all the fields of modern perfumery, such as fine perfumery or functional perfumery. Indeed, the invention's compounds may be advantageously employed in fine or functional perfumery to achieve a more controlled deposition, and consequent release, of odoriferous compounds. For example, the polymers according to the invention, owing to a good substantivity, a low volatility and a well controlled release of odoriferous molecules, can be incorporated in any application requiring the effect of rapid or prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin.

Consequently, a perfuming consumer product comprising, as a perfuming ingredient, at least one invention's polymer as defined above, is also an object of the present invention.

For the sake of clarity, it has to be mentioned that, by "perfuming consumer product" it is meant a consumer product which is expected to deliver at least a pleasant perfuming effect to the surface to which it is applied (e.g. skin, hair, textile, or hard surface). In other words, a perfuming consumer product according to the invention is a perfumed consumer product which comprises the functional formulation, as well as optionally additional benefit agents, corresponding to the desired consumer product, e.g. a detergent or an air freshener, and an olfactive effective amount of at least one invention's polymer.

The nature and type of the constituents of the perfuming consumer product do not warrant a more detailed description here, which in any case would not be exhaustive, the skilled person being able to select them on the basis of its general knowledge and according to the nature and the desired effect of said product.

Non-limiting examples of suitable perfuming consumer products can be a perfume, such as a fine perfume, a cologne or an after-shave lotion; a fabric care product, such as a solid or liquid detergent or a unidose detergent (like a powder tablet, a liquid unidose or a multichamber unidose detergent), a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or a hard-surface detergent.

According to anyone of the invention's embodiments, said perfuming consumer product is a perfume, fabric detergent or a softener base.

According to anyone of the invention's embodiments, said perfuming consumer product is a rinse-off product (i,e, a product which requires an rinsing step), such as a shampoo, a rinse-off conditioner or a liquid or powder detergent.

As mentioned above, the polymers according to the invention, can impart a fragrance and a freshness to a treated surface which will last well beyond the rinsing and/or drying processes.

A further aspect of the present invention is a method to confer, enhance, improve or modify the odor properties of a surface, which method comprises depositing on said surface, or washing said surface with, an effective amount of at least one polymer according to the invention. Said surface can be any one, and one can cite as non-limiting examples, textiles, hard surfaces, hair and skin, and in particularly synthetic fibers, such as polyesters, and hair.

Some of the above-mentioned perfuming consumer products may represent an aggressive medium for the invention's compound, so that it may be necessary to protect the latter from premature decomposition, for example by encapsulation.

Typical examples of fabric detergents or softener compositions into which the compounds of the invention can be incorporated are described in WO 97/34986, in WO 2012/113746 or in U.S. Pat. Nos. 4,137,180 and 5,236,615 or EP 799 885. Other typical detergent and softening compositions which can be used are described in works such as Ullman's Encyclopedia of Industrial Chemistry, vol. A8, pages 315-448 (1987) and vol. A25, pages 747-817 (1994); Flick, Advanced Cleaning Product Formulations, Noye Publication, Park Ridge, N.J. (1989); Showell, in Surfactant Science Series, vol. 71: Powdered Detergents, Marcel Dekker, New York (1988); Proceedings of the World Conference on Detergents (4th, 1998, Montreux, Switzerland), AOCS print.

The proportions in which the compounds according to the invention can be incorporated into the various aforementioned products or compositions vary within a wide range of values. These values are dependent on the nature of the product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 20% by weight, or even more, of the invention's compound based on the weight of the composition into which they are incorporated. Concentrations lower than these, such as in the order of 0.001% to 10% by weight, can be used when this compound is applied directly in the perfuming of the various perfuming consumer products mentioned hereinabove.

Another object of the present invention relates to a method for the perfuming of a surface or to a method for intensifying or prolonging the diffusion effect of the characteristic fragrance of an odoriferous ingredient on a surface, characterized in that said surface is treated in the presence of an invention's compound. Suitable surfaces are, in particular, textiles, hard surfaces, hair and skin.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) on a Bruker DPX 400 spectrometer with 400 MHz for $^1$H and 100 MHz for $^{13}$C, the chemical displacements δ are indicated in ppm with respect to the TMS as standard, the coupling constants J are expressed in Hz.

Commercially available reagents and solvents were used without further purification, if not stated otherwise. IR Spectra: Perkin Elmer Spectrum One FTIR spectrometer, ν in cm$^{-1}$. Size exclusion chromatography (SEC) analyses were carried out at room temperature (ca. 22° C.) on a Viscotek GPC max VE 2001 GPC Solvent Sample Module connected to a Viscotek UV detector 2500, a Viscotek VE3580 RI detector and a Viscotek-270-Dual-Detector viscometer. Samples were eluted from Waters Styragel HR 4E and HP 5 (7.8×300 mm) columns at a flow rate of 1.0 mL min$^{-1}$ with tetrahydrofuran (THF, HPLC-grade). Universal calibrations were performed using commercial poly(styrene) standards. The polymer standard (ca. 40 mg) was accurately weighed and dissolved in THF (10 mL); then these solutions (100 μL) were injected for the calibration. For the molecular weights of the polymers determined by SEC, M$_w$ stands for "weight average molecular weight" and M$_n$ stands for "number average molecular weight". Viscosity measurements were performed on a Bohlin C-VOR 150 rheometer equipped with 4/40 cone/plate geometry (diameter 40 mm, angle 4°) at 25° C. and a shear rate from 1/s to 100/s rpm. The viscosity measured at a shear rate of 10/s rpm was reported in Table 1 of Example 1. In the examples by "conversion", we define the conversion as the ratio of the addition of perfume molecule P on the functional monomer A' forming the repeating unit I in the polymer of the present invention. A complete conversion corresponds to a complete addition of molecule P to monomer A' in the final copolymer.

In the examples by "yield", we define the yield as the weight ratio between the mass of copolymer recovered at the end of the reaction and the expected theoretical mass of copolymer, as a function of the conversion defined above.

Example 1

Preparation of Polymers According to the Invention

General Protocol for the Preparation of ({3-mercaptopropyl}methyl)siloxane Polymers 1-41 with Various Co-Monomers and Different Odoriferous α,β-Unsaturated Ketones or Aldehydes In a 50 mL round-bottomed flask, (3-mercaptopropyl)(methyl)dimethoxysilane (compound of formula (i), x mmol), and optionally (dimethyl)diethoxysilane or (methyl)(phenyl)diethoxysilane or (n-octadecyl)(methyl)dimethoxysilane (compound of formula (ii), y mmol), and/or optionally ((N,N-dimethylamino)-3-propyl)(methyl)dimethoxysilane or (3-mercaptopropyl)(methyl)dimethoxysilane (compound of formula (iii), p mmol), and/or optionally (trimethyl)ethoxysilane (compound of formula (iv), (v) or (vi), z mmol) were dissolved altogether in water (n mmol) and sodium hydroxide (1.3 wt % with respect to the amount of water) to give an emulsion (Table 1). The reaction mixture was stirred at room temperature for 3 h. Ethanol, methanol and possible residual water were removed by evaporation under reduced pressure. An odoriferous α,β-unsaturated ketone or aldehyde (formula P, x mmol) and 2,3,4,6,7,8,9,10-octahydropyrimido[1,2-a]azepine (DBU, 5 mol % with respect to the amount of P) were added and the reaction mixture was stirred at room temperature for 3 h to give a viscous oil. This oil was diluted in ethyl acetate (10 mL) and washed with aq. NaCl (5 M, 2×10 mL). The aqueous layer was back-extracted with ethyl acetate (1×10 mL). The organic layers were combined and dried with MgSO$_4$, filtered and dried under vacuum at 50° C. overnight to give a viscous liquid.

Copolymers 15 and 16 were further functionalized. In a 100 mL round-bottomed flask, copolymers 15 or 16 were dissolved in ethyl acetate to give a colorless solution. To each of the two copolymers, 1-bromohexadecane (to give copolymers 18 and 19) or dimethyl sulfate (to give copolymers 20 and 21) (p mmol, Table 1) was added. The reaction mixture was stirred at room temperature for 4 h or at 60° C. overnight. The solvent was evaporated under reduced pressure. Complete conversion was observed by NMR.

TABLE 1

Composition and specifications of copolymers 1-41.

| Copolymer | α,β-unsaturated ketone or aldehyde P | Compound of formula (i) (x mmol) | Compound of formula (ii) (y mmol, Dimethyl)diethoxysilane R$^{11}$ = Me) | Compound of formula (iii) (p mmol) | Compound of formula (iv) to (vi) (Terminal group, z mmol) | Water (n mmol) | Terminal group | I/Tot (mol %) | M$_w$ (Da) | Viscosity (Pa · s) |
|---|---|---|---|---|---|---|---|---|---|---|
| 1 | P-1 | 40 | | | 4 | 84 | SiMe$_3$ | 100 | 9400 | 32.2 |
| 2 | P-1 | 25 | 5 | | 2.5 | 62.5 | SiMe$_3$ | 83 | 6800 | 23.5 |
| 3 | P-1 | 25 | 5 | | 15 | 75 | SiMe$_3$ | 83 | 3900 | 1.6 |
| 4 | P-1 | 25 | 5 | | 30 | 90 | SiMe$_3$ | 83 | 2000 | 2.3 |
| 5 | P-1 | 25 | 25 | | 5 | 105 | SiMe$_3$ | 50 | 18000 | 15.6 |
| 6 | P-1 | 25 | 5 | | | 50 | H, Me or Et | 83 | 3200 | 12.8 |
| 7 | P-1 | 25 | 5 | | | 20 | Me or Et | 83 | 2000 | 0.8 |
| 8 | P-1 | 80 | | | | 160 | H | 100 | 5800 | 55.7 |
| 9 | P-1 | 25 | 5 | | | 60 | H | 83 | 14000 | 83.9 |
| 10 | P-1 | 25 | 25 | | | 100 | H | 50 | 13000 | 17.3 |
| 11 | P-3 | 55.9 | | | | 112 | H | 100 | 17000 | n.m. |
| 12 | P-1 | 25 | 5 | | | 60 | H | 83 | 35000 | n.m. |
| 14 | P-3 | 25 | 25 | | | 100 | H | 50 | 39000 | n.m. |
| 15 | P-1 | 25 | 20 | 5$^{e)}$ | | 100 | H | 50 | 2500 | 9.3 |
| 16 | P-1 | 25 | | 25$^{e)}$ | | 100 | H | 50 | 1200 | 6.1 |
| 17 | P-1 | 25 | 5 | 5$^{e)}$ | 15 | 85 | SiMe$_3$ | 71 | 2500 | 2.4 |
| 18 | P-1 | 25 | 20 | 5$^{e)}$ | | 100 | H | 50 | 1900 | n.m. |

TABLE 1-continued

Composition and specifications of copolymers 1-41.

| Co-polymer | α,β-unsaturated ketone or aldehyde P | Compound of formula (i) (x mmol) | Compound of formula (ii) (y mmol, Dimethyl)diethoxysilane $R^{11}$ = Me) | Compound of formula (iii) (p mmol) | Compound of formula (iv) to (vi) (Terminal group, z mmol) | Water (n mmol) | Terminal group | I/Tot (mol %) | $M_w$ (Da) | Viscosity (Pa · s) |
|---|---|---|---|---|---|---|---|---|---|---|
| 19 | P-1 | 25 | | 25[e] | | 100 | H | 50 | n.m. | n.m. |
| 20 | P-1 | 25 | 20 | 50[f] | | 100 | H | 50 | 6500 | n.m. |
| 21 | P-1 | 25 | | 25[f] | | 100 | H | 50 | 1300 | n.m. |
| 22 | P-1 | 21 | | | | 19 | Me or Et | 100 | 3900 | 10.8 |
| 23 | P-1 | 39 | | 8.4[d] | | 51.4 | Me or Et | 82 | 6200 | 60.0 |
| 24 | P-1 | 47.4 | 9.5 | | | 51.4 | Me or Et | 83 | 3000 | 3.6 |
| 25 | P-1 | 18.7 | | 18.7[d] | | 33.7 | Me or Et | 50 | 4600 | 5.7 |
| 26 | P-1 | 28.5 | 28.5 | | | 51.4 | Me or Et | 50 | 3000 | 1.2 |
| 27 | P-1 | 19 | 38 | | | 51.4 | Me or Et | 33 | 4800 | 2.2 |
| 28 | P-1 | 47.4 | 9.7[a] | | | 51.4 | Me or Et | 83 | 3100 | 7.8 |
| 29 | P-1 | 47.4 | 9.7[b] | | | 51.4 | Me or Et | 83 | 3600 | 2.8 |
| 30 | P-3 | 48.4 | 9.7 | | | 97 | H, Me or Et | 83 | 3600 | 19.1 |
| 31 | P-1 | 48.4 | 9.7 | | 29 | 145 | SiMe3 | 83 | 2600 | 1.2 |
| 32 | P-1 | 48.4 | 9.7 | | | 97 | H, Me or Et | 83 | 4300 | 8.2 |
| 33 | P-1 | 48.4 | 9.7 | | | 97 | H, Me or Et | 83 | 2900 | 5.1 |
| 34 | P-2 | 48.4 | 9.7 | | | 97 | H, Me or Et | 83 | 3100 | 6.2 |
| 35 | P-7 | 48.4 | 9.7 | | | 97 | H, Me or Et | 83 | 3100 | 5.1 |
| 36 | P-7 | 47.5 | 9.4 | | | 95 | H, Me or Et | 83 | 4800 | 24.1 |
| 37 | P-4 | 21.1 | 4.2 | | | 22.8 | Me or Et | 83 | 2300 | n.m. |
| 38[h] | P-4 | 21.1 | 21 | | | 38 | Me or Et | 50 | 4000 | 0.9 |
| 39[g] | P-2 | 48.4 | 9.7 | | | 97 | H, Me or Et | 83 | 6500 | 8.4 |
| 40[h] | P-4 | 29.1 | | | | 25.7 | Me or Et | 100 | 4700 | 1.1 | n.m. = not measured;
[a]$R^{11}$ = Me and Ph;
[b]$R^{11}$ = Me and $C_{18}H_{37}$;
[c]R = —$(CH_2)_3$—$N(Me)_2$;
[d]R = —$(CH_2)_3$—SH;
[e]R = —$(CH_2)_3$—$N^+(C_{16}H_{33})(Me)_2Br^-$;
[f]R = —$(CH_2)_3$—$N^+(Me)_3MeSO_4^-$;
[g]no DBU;
[h]presence of citral in the copolymer.

Characterization of copolymers releasing (±)-(E)-(1RS, 2SR)-1-(2,6,6-trimethylcyclohex-3-enyl)but-2-en-1-one or (±)-trans-δ-damascone of formula P-1.

Copolymer 1: Yield (Y)=95%. Conversion=100%. $M_w$=9400 Da. $M_n$=6500 Da.

$^1$H-NMR: 5.52 (m, 1H), 5.44 (m, 1H), 3.28 (m, 1H), 2.89 (m, 1H), 2.71 (m, 2H), 2.56 (m, 2H), 2.54 (m, 1H), 2.51 (m, 1H), 2.22 (m, 1H), 1.97 (m, 1H), 1.69 (m, 1H), 1.65 (m, 1H), 1.59 (m, 2H), 1.29 (m, 3H), 0.98 (m, 3H), 0.95 (m, 3H), 0.89 (m, 3H), 0.62 (m, 2H), 0.13 (m, 0.3H), 0.08 (m, 3H); $^{13}$C-NMR: 212.3 (s), 131.8 (d), 124.2 (d), 62.9 (d), 55.3 (t), 41.8 (t), 34.4 (d), 34.3 (d), 34.2 (t), 33.2 (s), 31.8 (d), 29.8 (q), 23.6 (t), 21.9 (q), 20.8 (q), 19.9 (q), 17.4 (t), −0.18 (q).

Copolymer 2: Y=99%. Conversion=100%. $M_w$=6800 Da. $M_n$=5100 Da.

$^1$H-NMR: 5.52 (m, 1H), 5.44 (m, 1H), 3.28 (m, 1H), 2.89 (m, 1H), 2.71 (m, 2H), 2.56 (m, 2H), 2.54 (m, 1H), 2.51 (m, 1H), 2.22 (m, 1H), 1.97 (m, 1H), 1.69 (m, 1H), 1.65 (m, 1H), 1.59 (m, 2.2H), 1.29 (m, 3H), 0.98 (m, 3H), 0.95 (m, 3H), 0.89 (m, 3H), 0.62 (m, 2H), 0.08 (m, 3.7H); $^{13}$C-NMR: 212.3 (s), 131.9 (d), 124.2 (d), 62.9 (d), 55.3 (t), 41.8 (t), 34.4 (d), 34.3 (d), 34.2 (t), 33.2 (s), 31.8 (d), 29.8 (q), 23.6 (t), 21.9 (q), 20.8 (q), 19.9 (q), 17.4 (t), −0.2 (q).

Copolymer 3: Y=75%. Conversion=100%. $M_w$=3900 Da. $M_n$=2500 Da.

$^1$H-NMR: 5.53 (m, 1H), 5.44 (m, 1H), 3.29 (m, 1H), 2.90 (m, 1H), 2.71 (m, 1H), 2.55 (m, 2H), 2.50 (m, 1H), 2.22 (m, 1H), 1.97 (m, 1H), 1.69 (m, 1H), 1.62 (m, 2H), 1.29 (m, 3H), 0.98 (m, 3H), 0.95 (m, 3H), 0.89 (m, 3H), 0.62 (m, 2H), 0.09 (m, 5H); $^{13}$C-NMR: 212.4 (s), 131.9 (d), 124.3 (d), 124.1 (d), 62.9 (d), 62.8 (d), 55.3 (t), 41.8 (t), 34.4 (d), 34.3 (t), 34.2 (t), 34.1 (d), 33.2 (s), 33.0 (s), 31.8 (d), 31.6 (d), 29.8 (q), 23.6 (t), 21.9 (q), 21.8 (q), 20.8 (q), 20.0 (q), 19.9 (q), 17.4 (t), 1.9 (q), 1.3 (q), −0.3 (q), −1.1 (q).

Copolymer 4: Y=80%. Conversion=100%. $M_w$=2000 Da. $M_n$=1600 Da.

$^1$H-NMR: 5.53 (m, 1H), 5.45 (m, 1H), 3.29 (m, 1H), 2.90 (m, 1H), 2.70 (m, 1H), 2.54 (m, 2H), 2.50 (m, 1H), 2.22 (m, 1H), 1.97 (m, 1H), 1.69 (m, 1H), 1.63 (m, 2H), 1.30 (m, 3H), 0.98 (m, 3H), 0.95 (m, 3H), 0.89 (m, 3H), 0.62 (m, 2H), 0.09 (m, 7H); $^{13}$C-NMR: 212.3 (s), 131.9 (d), 124.3 (d), 124.1 (d), 63.0 (d), 62.8 (d), 55.3 (t), 41.8 (t), 34.4 (t), 34.3 (d), 34.2 (t), 34.1 (d), 33.2 (s), 33.0 (s), 31.8 (d), 31.6 (d), 29.8 (q), 23.6 (t), 21.9 (q), 21.8 (q), 20.8 (q), 20.0 (q), 19.9 (q), 17.4 (t), 1.9 (q), 1.3 (q), −0.3 (q), −1.0 (q).

Copolymer 5: Y=94%. Conversion=100%. $M_w$=18000 Da. $M_n$=9300 Da.

$^1$H-NMR: 5.52 (m, 1H), 5.44 (m, 1H), 3.28 (m, 1H), 2.89 (m, 1H), 2.71 (m, 2H), 2.56 (m, 2H), 2.54 (m, 1H), 2.51 (m, 1H), 2.22 (m, 1H), 1.97 (m, 1H), 1.71 (m, 1H), 1.66 (m, 1H), 1.61 (m, 2H), 1.29 (m, 3H), 0.98 (m, 3H), 0.95 (m, 3H), 0.89 (m, 3.6H), 0.62 (m, 2H), 0.08 (m, 9H); $^{13}$C-NMR: 212.2 (s), 131.9 (d), 124.2 (d), 62.9 (d), 55.3 (t), 41.8 (d), 34.4 (d), 34.3 (d), 34.2 (t), 33.1 (s), 31.8 (d), 29.8 (q), 23.6 (t), 21.8 (q), 20.8 (q), 19.9 (q), 17.3 (t), 1.2 (q), −0.3 (q).

Copolymer 6: Y=92%. Conversion=100%. $M_w$=3200 Da. $M_n$=2400 Da.

$^1$H-NMR: 5.53 (m, 1H), 5.45 (m, 1H), 3.29 (m, 1H), 2.90 (m, 1H), 2.71 (m, 1H), 2.56 (m, 2H), 2.50 (m, 1H), 2.22 (m, 1H), 1.97 (m, 1H), 1.69 (m, 1H), 1.63 (m, 2H), 1.29 (m, 3H), 0.98 (m, 3H), 0.95 (m, 3H), 0.89 (m, 3H), 0.63 (m, 2H), 0.08 (m, 4H); $^{13}$C-NMR: 212.3 (s), 131.8 (d), 124.2 (d), 124.1 (d), 62.9 (d), 62.8 (d), 55.3 (t), 41.8 (t), 34.4 (t), 34.3 (d), 34.2 (t), 34.1 (d), 33.2 (s), 33.0 (s), 31.8 (d), 31.6 (d), 29.8 (q), 23.6 (t), 21.9 (q), 21.7 (q), 20.8 (q), 20.0 (q), 19.9 (q), 17.4 (t), 1.3 (q), −0.2 (q), −1.1 (q).

Copolymer 7: Y=89%. Conversion=100%. $M_w$=2000 Da. $M_n$=1600 Da.

$^1$H-NMR: 5.53 (m, 1H), 5.45 (m, 1H), 3.47 (m, 1H), 3.29 (m, 1H), 2.90 (m, 1H), 2.70 (m, 1H), 2.55 (m, 2H), 2.50 (m, 1H), 2.22 (m, 1H), 1.97 (m, 1H), 1.70 (m, 1H), 1.64 (m, 2H), 1.29 (m, 3H), 1.19 (m, 1H), 0.98 (m, 3H), 0.95 (m, 3H), 0.89 (m, 3H), 0.63 (m, 2H), 0.10 (m, 4H); $^{13}$C-NMR: 212.3 (s), 131.8 (d), 124.2 (d), 124.1 (d), 62.9 (d), 62.8 (d), 55.4 (t), 49.9 (q), 41.8 (t), 34.4 (t), 34.3 (d), 34.2 (t), 34.1 (d), 33.2 (s), 33.0 (s), 31.8 (d), 31.6 (d), 29.8 (q), 23.6 (t), 21.9 (q), 21.7 (q), 20.8 (q), 20.0 (q), 19.9 (q), 17.3 (t), 15.2 (t), −0.3 (q), −3.0 (q).

Copolymer 8: Y=73%. Conversion=100%. $M_w$=5800 Da. $M_n$=3500 Da.

$^1$H-NMR: 5.52 (m, 1H), 5.44 (m, 1H), 3.28 (m, 1H), 2.89 (m, 1H), 2.71 (m, 2H), 2.56 (m, 2H), 2.54 (m, 1H), 2.51 (m, 1H), 2.22 (m, 1H), 1.97 (m, 1H), 1.69 (m, 1H), 1.65 (m, 1H), 1.59 (m, 2H), 1.29 (m, 3H), 0.98 (m, 3H), 0.95 (m, 3H), 0.89 (m, 3H), 0.62 (m, 2H), 0.08 (m, 3H); $^{13}$C-NMR: 212.2 (s), 131.9 (d), 124.2 (d), 62.8 (d), 55.3 (t), 41.9 (t), 34.8 (d), 34.4 (d), 34.2 (t), 33.1 (s), 31.8 (d), 29.8 (q), 23.6 (t), 21.9 (q), 20.7 (q), 19.9 (q), 17.4 (t), −0.16 (q).

Copolymer 9: Y=91%. Conversion=100%. $M_w$=14000 Da. $M_n$=7500 Da.

$^1$H-NMR: 5.52 (m, 1H), 5.44 (m, 1H), 3.28 (m, 1H), 2.89 (m, 1H), 2.71 (m, 2H), 2.56 (m, 2H), 2.54 (m, 1H), 2.51 (m, 1H), 2.22 (m, 1H), 1.97 (m, 1H), 1.69 (m, 1H), 1.65 (m, 1H), 1.59 (m, 2H), 1.29 (m, 3H), 0.98 (m, 3H), 0.95 (m, 3H), 0.89 (m, 3H), 0.62 (m, 2H), 0.08 (m, 4H); $^{13}$C-NMR: 212.2 (s), 131.9 (d), 124.2 (d), 62.8 (d), 55.3 (t), 41.9 (t), 34.8 (d), 34.4 (d), 34.2 (d), 33.1 (s), 31.8 (d), 29.8 (q), 23.6 (t), 21.9 (q), 20.7 (q), 19.9 (q), 17.4 (t), 1.3 (q), −0.2 (q).

Copolymer 10: Y=93%. Conversion=100%. $M_w$=13000 Da. $M_n$=7400 Da.

$^1$H-NMR: 5.52 (m, 1H), 5.44 (m, 1H), 3.28 (m, 1H), 2.89 (m, 1H), 2.71 (m, 2H), 2.56 (m, 2H), 2.54 (m, 1H), 2.51 (m, 1H), 2.22 (m, 1H), 1.97 (m, 1H), 1.69 (m, 1H), 1.65 (m, 1H), 1.59 (m, 2H), 1.29 (m, 3H), 0.98 (m, 3H), 0.95 (m, 3H), 0.89 (m, 3H), 0.62 (m, 2H), 0.08 (m, 8H); $^{13}$C-NMR: 212.2 (s), 131.9 (d), 124.2 (d), 62.8 (d), 55.3 (t), 41.9 (t), 34.8 (d), 34.4 (d), 34.2 (d), 33.1 (s), 31.8 (d), 29.8 (q), 23.6 (t), 21.9 (q), 20.7 (q), 19.9 (q), 17.4 (t), 1.2 (q), −0.3 (q).

Copolymer 15: Y=94%. Conversion=100%. $M_w$=2500 Da. $M_n$=1900 Da.

$^1$H-NMR: 5.52 (m, 1H), 5.44 (m, 1H), 3.28 (m, 1H), 2.89 (m, 1H), 2.71 (m, 2H), 2.56 (m, 2.2H), 2.54 (m, 1H), 2.51 (m, 1H), 2.22 (m, 1H), 2.21 (m, 1H), 1.97 (m, 1H), 1.69 (m, 1H), 1.65 (m, 1H), 1.59 (m, 2H), 1.29 (m, 3H), 0.98 (m, 3H), 0.95 (m, 3H), 0.89 (m, 4H), 0.62 (m, 2.4H), 0.08 (m, 9H); $^{13}$C-NMR: 212.3 (s), 131.8 (d), 124.1 (d), 62.9 (d), 55.3 (t), 45.4 (q), 41.8 (t), 34.8 (d), 34.4 (t), 34.2 (d), 33.1 (s), 31.8 (d), 29.8 (q), 23.6 (t), 21.9 (q), 20.7 (q), 19.9 (q), 17.4 (t), 1.2 (q), −0.3 (q).

Copolymer 16: Y=91%. Conversion=100%. $M_w$=1200 Da. $M_n$=1000 Da.

$^1$H-NMR: 5.52 (m, 1H), 5.44 (m, 1H), 3.28 (m, 1H), 2.89 (m, 1H), 2.71 (m, 2H), 2.56 (m, 2H), 2.54 (m, 1H), 2.51 (m, 1H), 2.22 (m, 1H), 2.21 (m, 6H), 1.97 (m, 1H), 1.69 (m, 1H), 1.65 (m, 1H), 1.59 (m, 4H), 1.29 (m, 3H), 0.98 (m, 3H), 0.95 (m, 3H), 0.89 (m, 3H), 0.62 (m, 2H), 0.08 (m, 6H); $^{13}$C-NMR: 212.3 (s), 131.8 (d), 124.1 (d), 63.0 (t), 62.8 (d), 55.3 (t), 45.3 (q), 41.9 (t), 34.4 (d), 34.3 (t), 34.2 (d), 33.1 (s), 31.8 (d), 29.8 (q), 23.6 (t), 21.9 (q), 21.1 (t), 20.7 (q), 19.9 (q), 17.4 (t), 15.1 (t), −0.3 (q), −0.6 (q), −1.0 (q).

Copolymer 17: Y=81%. Conversion=100%. $M_w$=2500 Da. $M_n$=1800 Da.

$^1$H-NMR: 5.52 (m, 1H), 5.45 (m, 1H), 3.29 (m, 1H), 2.90 (m, 1H), 2.71 (m, 1H), 2.55 (m, 3H), 2.22 (m, 2.5H), 1.96 (m, 1H), 1.65 (m, 1H), 1.29 (m, 3H), 0.98 (m, 3H), 0.95 (m, 3H), 0.89 (m, 4H), 0.62 (m, 2H), 0.50 (m, 0.4H), 0.11 (m, 6H); $^{13}$C-NMR: 212.3 (s), 131.8 (d), 124.2 (d), 124.1 (d), 62.9 (d), 62.8 (d), 55.4 (t), 55.3 (t), 45.5 (q), 45.0 (q), 41.8 (t), 34.3 (t), 33.2 (s), 33.1 (s), 31.8 (d), 31.6 (d), 31.4 (d), 30.0 (q), 29.8 (q), 23.6 (t), 21.9 (q), 21.8 (q), 20.9 (q), 20.8 (q), 19.9 (q), 17.4 (t), 15.1 (t), 1.9 (q), 1.3 (q), −0.3 (q).

Copolymer 18: $M_w$=1900 Da. $M_n$=1400 Da.

$^1$H-NMR: 5.53 (m, 1H), 5.44 (m, 1H), 3.47 (m, 0.2H), 3.28 (m, 1H), 2.89 (m, 1H), 2.70 (m, 2H), 2.56 (m, 2.2H), 2.54 (m, 1H), 2.51 (m, 1H), 2.22 (m, 1H), 2.21 (m, 1H), 1.96 (m, 1H), 1.86 (m, 1H), 1.71 (m, 1H), 1.66 (m, 1H), 1.61 (m, 2H), 1.28 (m, 3H), 1.26 (m, 5H), 0.98 (m, 3H), 0.95 (m, 3H), 0.89 (m, 4.5H), 0.63 (m, 2H), 0.08 (m, 9H); $^{13}$C-NMR: 212.3 (s), 131.8 (d), 124.1 (d), 62.9 (d), 55.3 (t), 45.4 (q), 41.8 (t), 34.4 (d), 34.2 (d), 34.0 (t), 33.0 (s), 31.7 (d), 29.8 (q), 29.7 (t), 29.4 (t), 28.8 (t), 28.2 (t), 23.6 (t), 22.9 (t), 22.7 (t), 21.9 (q), 20.7 (q), 19.9 (q), 18.2 (q), 17.3 (t), 14.1 (q), 1.2 (q), −0.3 (q).

Copolymer 19:

$^1$H-NMR: 5.53 (m, 1H), 5.45 (m, 1H), 3.84 (m, 1H), 3.51 (m, 2H), 3.29 (m, 5H), 2.89 (m, 1H), 2.70 (m, 2H), 2.56 (m, 2.2H), 2.54 (m, 1H), 2.51 (m, 1H), 2.21 (m, 3H), 1.96 (m, 1H), 1.86 (m, 1H), 1.72 (m, 2H), 1.68 (m, 1H), 1.61 (m, 2H), 1.36 (m, 3H), 1.26 (m, 27H), 0.98 (m, 3H), 0.94 (m, 6H), 0.89 (m, 6H), 0.64 (m, 4H), 0.20 (m, 6H); $^{13}$C-NMR: 212.4 (s), 131.7 (d), 124.3 (d), 62.9 (d), 60.4 (s), 60.2 (s), 55.3 (t), 50.8 (q), 50.3 (q), 45.2 (q), 41.8 (t), 34.4 (t), 34.2 (d), 34.1 (t), 33.2 (s), 33.0 (s), 32.9 (t), 31.9 (t), 31.8 (d), 31.6 (d), 29.8 (q), 29.7 (t), 29.5 (t), 29.4 (t), 29.3 (t), 28.8 (t), 28.2 (t), 26.4 (t), 23.6 (t), 22.9 (t), 22.7 (t), 21.9 (q), 20.8 (q), 19.9 (q), 18.2 (q), 17.3 (t), 16.9 (t), 14.1 (q), 1.2 (q), −0.2 (q), −0.5 (q).

Copolymer 20: $M_w$=6500 Da. $M_n$=2400 Da.

$^1$H-NMR ((CD$_3$)$_2$CO): 5.52 (m, 1H), 5.44 (m, 1H), 3.37 (m, 1H), 3.28 (m, 1H), 2.99 (m, 4H), 2.78 (m, 1H), 2.48 (m, 1H), 2.33 (m, 1H), 1.99 (m, 1H), 1.72 (m, 1H), 1.69 (m, 1H), 1.30 (m, 3H), 1.02 (m, 3H), 0.94 (m, 3H), 0.91 (m, 3H), 0.73 (m, 2H), 0.17 (m, 8H); $^{13}$C-NMR ((CD$_3$)$_2$CO): 212.3 (s), 132.8 (d), 125.0 (d), 63.1 (d), 56.0 (t), 53.6 (d), 42.3 (t), 34.9 (d), 34.8 (d), 34.7 (t), 33.7 (s), 32.5 (d), 30.1 (q), 24.5 (t), 22.4 (q), 21.1 (q), 20.2 (q), 18.0 (t), 1.7 (q), 1.0 (q).

Copolymer 21: $M_w$=1300 Da. $M_n$=1200 Da.

$^1$H-NMR ((CD$_3$)$_2$CO): 5.55 (m, 1H), 5.48 (m, 1H), 3.66 (m, 2H), 3.56 (s, 3H), 3.33 (m, 11H), 2.95 (m, 3H), 2.79 (m, 2H), 2.63 (m, 3H), 2.48 (m, 1H), 2.34 (m, 1H), 1.99 (m, 3H), 1.70 (m, 4H), 1.30 (m, 5H), 1.03 (m, 3H), 0.94 (m, 6H), 0.90 (m, 3H), 0.73 (m, 5H), 0.50 (m, 2H), 0.20 (m, 8H); $^{13}$C-NMR ((CD$_3$)$_2$CO): 212.5 (s), 132.6 (d), 125.1 (d), 69.1 (t), 62.8 (d), 56.0 (t), 53.3 (d), 42.4 (t), 34.9 (d), 34.7 (d), 34.6 (t), 33.7 (s), 31.8 (d), 30.07 (q), 24.6 (t), 22.4 (q), 21.1 (t), 20.2 (q), 19.9 (t), 17.9 (t), 14.5 (t), 0.2 (q), −0.3 (q).

Copolymer 22: Y=98%. Conversion=95%. $M_w$=3900 Da. $M_n$=2500 Da.

$^1$H-NMR: 5.53 (m, 1H), 5.45 (m, 1H), 3.47 (m, 1.3H), 3.29 (m, 1H), 2.90 (m, 0.5H), 2.70 (m, 1H), 2.55 (m, 2.5H), 2.50 (m, 1H), 2.24 (m, 1H), 1.97 (m, 1H), 1.69 (m, 1H), 1.62 (m, 1H), 1.30 (m, 3H), 1.19 (m, 1H), 0.99 (m, 3H), 0.94 (m, 3H), 0.89 (m, 3H), 0.63 (m, 2H), 0.10 (m, 3H); $^{13}$C-NMR: 212.3 (s), 131.9 (d), 124.3 (d), 124.1 (d), 62.9 (d), 62.8 (d), 55.4 (t), 49.9 (q), 41.9 (t), 34.4 (t), 34.3 (t), 34.2 (d), 34.1

(t), 33.2 (s), 33.0 (s), 31.8 (d), 31.5 (d), 29.8 (q), 23.6 (t), 21.9 (q), 21.7 (q), 20.8 (q), 20.0 (q), 19.9 (q), 17.3 (t), 15.0 (t), −0.2 (q), −3.0 (q).

Copolymer 23: Y=93%. Conversion=100% (0.83 eq.). $M_w$=6200 Da. $M_n$=2900 Da.

$^1$H-NMR: 5.52 (m, 0.8H), 5.44 (m, 0.8H), 3.47 (m, 0.3H), 3.29 (m, 0.8H), 2.91 (m, 0.4H), 2.71 (m, 0.8H), 2.57 (m, 3.2H), 2.22 (m, 0.8H), 1.97 (m, 0.8H), 1.70 (m, 0.8H), 1.63 (m, 2H), 1.30 (m, 2.5H), 0.98 (m, 2.5H), 0.95 (m, 2.5H), 0.89 (m, 2.5H), 0.64 (m, 2H), 0.09 (m, 3H); $^{13}$C-NMR: 212.3 (s), 131.8 (d), 124.2 (d), 124.1 (d), 62.9 (d), 62.8 (d), 55.4 (t), 55.3 (t), 50.0 (q), 41.7 (t), 34.4 (d), 34.3 (t), 34.2 (d), 34.1 (t), 33.2 (s), 33.0 (s), 31.8 (d), 31.6 (d), 29.8 (q), 27.9 (t), 27.8 (t), 23.6 (t), 22.0 (q), 21.9 (q), 21.8 (q), 21.7 (q), 20.7 (q), 20.0 (q), 19.9 (q), 19.8 (q), 17.4 (t), 17.2 (t), 16.9 (t), 15.0 (t), −0.2 (q), −0.6 (q), −3.0 (q).

Copolymer 24: Y=99%. Conversion=91%. $M_w$=3000 Da. $M_n$=2000 Da.

$^1$H-NMR: 5.54 (m, 0.9H), 5.45 (m, 0.9H), 3.74 (m, 0.1H), 3.47 (m, 1H), 3.29 (m, 1H), 2.90-2.50 (m, 0.9H), 2.70 (m, 0.9H), 2.55 (m, 2H), 2.22 (m, 0.9H), 1.97 (m, 0.9H), 1.69 (m, 0.9H), 1.64 (m, 2H), 1.29 (m, 3H), 0.98 (m, 2.9H), 0.95 (m, 2.9H), 0.89 (m, 2.9H), 0.63 (m, 2H), 0.10 (m, 4H); $^{13}$C-NMR: 212.3 (s), 131.8 (d), 124.2 (d), 124.1 (d), 62.9 (d), 62.8 (d), 55.3 (t), 41.7 (t), 34.4 (t), 34.3 (t), 34.2 (d), 34.1 (t), 33.2 (s), 33.0 (s), 31.8 (d), 31.5 (d), 29.8 (q), 23.5 (t), 21.8 (q), 21.7 (q), 20.7 (q), 19.9 (q), 19.8 (q), 17.3 (t), 16.8 (t), 15.0 (t), 1.3 (q), −0.3 (q), −3.0 (q).

Copolymer 25: Conversion=100% (0.50 eq.). $M_w$=4600 Da. $M_n$=2700 Da.

$^1$H-NMR: 5.52 (m, 0.5H), 5.44 (m, 0.5H), 3.29 (m, 0.5H), 2.90 (m, 0.2H), 2.71 (m, 0.8H), 2.56 (m, 1.5H), 2.22 (m, 0.5H), 1.97 (m, 0.5H), 1.70 (m, 0.5H), 1.67 (m, 2H), 1.37 (m, 0.5H), 1.28 (m, 1.5H), 0.98 (m, 1.5H), 0.95 (m, 1.5H), 0.89 (m, 1.5H), 0.64 (m, 2H), 0.10 (m, 3H); $^{13}$C-NMR: 212.4 (s), 212.2 (s), 131.8 (d), 124.2 (d), 124.1 (d), 62.9 (d), 55.3 (t), 41.7 (t), 34.4 (t), 34.2 (d), 33.2 (s), 33.1 (s), 31.8 (d), 31.6 (d), 29.9 (q), 23.6 (t), 21.9 (q), 21.8 (q), 21.7 (q), 20.8 (q), 20.0 (q), 19.9 (q), 17.4 (t), 16.9 (t), 14.2 (q), −0.3 (q), −0.6 (q), −1.0 (q).

Copolymer 26: Y=99%. Conversion=95%. $M_w$=3000 Da. $M_n$=2000 Da.

$^1$H-NMR: 5.53 (m, 1H), 5.46 (m, 1H), 3.74 (m, 0.6H), 3.47 (m, 0.6H), 3.29 (m, 1H), 2.89 (m, 0.5H), 2.70 (m, 1H), 2.55 (m, 2.5H), 2.52 (m, 1H), 2.21 (m, 1H), 1.97 (m, 1H), 1.69 (m, 1H), 1.63 (m, 2H), 1.29 (m, 3H), 1.21 (m, 1H), 0.98 (m, 3H), 0.95 (m, 3H), 0.89 (m, 3H), 0.63 (m, 2H), 0.08 (m, 9H); $^{13}$C-NMR: 212.3 (s), 131.8 (d), 124.2 (d), 124.1 (d), 62.9 (d), 62.8 (d), 55.3 (t), 41.7 (t), 34.3 (t), 34.2 (d), 33.2 (s), 33.0 (s), 31.8 (d), 31.5 (d), 29.8 (q), 23.6 (t), 21.8 (q), 21.7 (q), 20.7 (q), 19.9 (q), 19.8 (q), 18.4 (s), 17.3 (t), 15.5 (t), 1.1 (q), 0.8 (q), −0.4 (q), −0.9 (q), −1.5 (q).

Copolymer 27: Y=98%. Conversion=93%. $M_w$=4800 Da. $M_n$=2100 Da.

$^1$H-NMR: 5.52 (m, 0.9H), 5.44 (m, 0.9H), 3.72 (m, 0.35H), 3.46 (m, 0.25H), 3.28 (m, 1H), 2.90 (m, 0.5H), 2.70 (m, 1H), 2.55 (m, 2.5H), 2.51 (m, 1H), 2.22 (m, 1H), 1.97 (m, 1H), 1.69 (m, 1H), 1.62 (m, 2H), 1.29 (m, 3H), 0.98 (m, 3H), 0.95 (m, 3H), 0.89 (m, 3H), 0.63 (m, 2H), 0.07 (m, 13H); $^{13}$C-NMR: 212.3 (s), 131.8 (d), 124.2 (d), 124.1 (d), 62.9 (d), 62.8 (d), 55.3 (t), 41.7 (t), 34.3 (t), 33.2 (s), 33.0 (s), 31.8 (d), 31.5 (d), 29.8 (q), 23.6 (t), 21.9 (q), 21.7 (q), 20.7 (q), 19.9 (q), 19.8 (q), 18.4 (s), 17.3 (t), 16.9 (t), 1.1 (q), 0.8 (q), −0.4 (q), −0.7 (q), −0.9 (q).

Copolymer 28: Y=99%. Conversion=98%. $M_w$=3100 Da. $M_n$=2000 Da.

$^1$H-NMR: 7.57 (m, 0.35H), 7.36 (m, 0.55H), 5.52 (m, 1H), 5.44 (m, 1H), 3.73 (m, 0.1H), 3.47 (m, 0.5H), 3.28 (m, 1H), 2.90 (m, 1H), 2.70 (m, 1H), 2.54 (m, 2.5H), 2.50 (m, 1H), 2.22 (m, 1H), 1.96 (m, 1H), 1.69 (m, 1H), 1.62 (m, 2H), 1.29 (m, 3H), 0.98 (m, 3H), 0.95 (m, 3H), 0.89 (m, 3H), 0.63 (m, 2H), 0.33 (m, 0.6H), 0.09 (m, 3H); $^{13}$C-NMR: 212.2 (s), 133.2 (d), 131.8 (d), 129.7 (d), 127.7 (d), 124.2 (d), 124.1 (d), 62.9 (d), 62.8 (d), 55.3 (t), 34.3 (d), 34.2 (d), 33.2 (s), 33.0 (s), 31.8 (d), 31.5 (d), 29.8 (q), 23.5 (t), 21.9 (q), 21.7 (q), 20.8 (q), 20.0 (q), 19.9 (q), 17.3 (t), 16.9 (t), 15.0 (t), −0.3 (q), −0.7 (q), −2.5 (q), −3.0 (q).

Copolymer 29: Y=99%. Conversion=95%. $M_w$=3600 Da. $M_n$=2500 Da.

$^1$H-NMR: 5.52 (m, 1H), 5.44 (m, 1H), 3.47 (m, 0.9H), 3.29 (m, 1H), 2.90 (m, 0.5H), 2.70 (m, 1H), 2.55 (m, 2.5H), 2.51 (m, 1H), 2.22 (m, 1H), 1.96 (m, 1H), 1.71 (m, 1H), 1.62 (m, 2H), 1.29 (m, 3H), 1.26 (s, 6H), 0.98 (m, 3H), 0.95 (m, 3H), 0.89 (m, 4H), 0.64 (m, 2H), 0.51 (m, 0.3H), 0.08 (m, 3.5H); $^{13}$C-NMR: 212.32 (s), 131.8 (d), 124.2 (d), 124.1 (d), 62.9 (d), 62.8 (d), 55.4 (t), 55.3 (t), 41.8 (t), 34.4 (t), 34.3 (d), 34.2 (d), 34.1 (t), 33.2 (s), 33.0 (s), 31.9 (d), 31.8 (d), 31.6 (d), 29.8 (q), 29.7 (q), 23.6 (t), 23.5 (t), 21.9 (q), 21.7 (q), 20.7 (q), 20.0 (q), 19.9 (q), 17.3 (t), 16.9 (t), 15.0 (t), 14.1 (q), −0.2 (q), −0.3 (q), −0.6 (q), −3.0 (q).

Characterization of copolymers releasing (E)-1-(2,6,6-trimethylcyclohexa-1,3-dien-1-yl)but-2-en-1-one or damascenone of formula P-1

Copolymer 31: Y=89%. Conversion=100%. $M_w$=2600 Da. $M_n$=1800 Da.

$^1$H-NMR: 5.83 (m, 1H), 5.78 (m, 1H), 3.47 (s, 0.18H), 3.35 (m, 1H), 2.89 (m, 1H), 2.72 (m, 1H), 2.57 (m, 2H), 2.08 (d, 2H), 1.72 (m, 3H), 1.64 (m, 2H), 1.62 (s, 1H), 1.34 (m, 3H), 1.08 (m, 6H), 0.64 (m, 2H), 0.09 (m, 7H); $^{13}$C-NMR: 207.6 (s), 141.6 (s), 128.1 (d), 127.7 (d), 127.4 (s), 52.9 (t), 39.7 (t), 34.3 (s), 33.9 (s), 26.2 (q), 23.5 (t), 21.8 (q), 19.1 (q), 17.4 (t), 1.9 (q), 1.3 (q), −0.3 (q), −1.1 (q).

Copolymer 32: Conversion=100%. $M_w$=4300 Da. $M_n$=2600 Da.

$^1$H-NMR: 5.83 (m, 1H), 5.78 (m, 1H), 3.47 (s, 0.24H), 3.36 (m, 1H), 2.89 (m, 1H), 2.72 (m, 1H), 2.58 (m, 2H), 2.08 (d, 2H), 1.72 (m, 3H), 1.64 (m, 3H), 1.34 (m, 3H), 1.08 (m, 6H), 0.64 (m, 2H), 0.09 (m, 4.5H); $^{13}$C-NMR: 207.6 (s), 141.6 (s), 128.1 (d), 127.7 (d), 127.5 (s), 52.9 (t), 39.8 (t), 34.3 (s), 33.9 (s), 26.2 (q), 23.5 (t), 21.8 (q), 19.1 (q), 17.4 (t), 1.9 (q), 1.3 (q), 0.8 (q), −0.3 (q), −1.0 (q).

Copolymer 33: Y=94%. Conversion=100%. $M_w$=2900 Da. $M_n$=2300 Da.

$^1$H-NMR: 5.83 (m, 1H), 5.78 (m, 1H), 3.47 (s, 0.21H), 3.36 (m, 1H), 2.89 (m, 1H), 2.72 (m, 1H), 2.58 (m, 2H), 2.08 (d, 2H), 1.72 (m, 3H), 1.64 (m, 3H), 1.34 (m, 3H), 1.08 (m, 6H), 0.64 (m, 2H), 0.09 (m, 4.1H); $^{13}$C-NMR: 207.5 (s), 141.6 (s), 128.1 (d), 127.6 (d), 127.4 (s), 53.0 (t), 39.7 (t), 34.3 (s), 33.8 (s), 26.2 (q), 23.5 (t), 21.9 (q), 19.1 (q), 17.4 (t), 16.8 (t), 1.9 (q), 1.3 (q), −0.3 (q).

Characterization of copolymers releasing (E)-4-(2,6,6-trimethylcyclohex-1-en-1-yl)but-3-en-2-one or β-ionone of formula P-2

Copolymer 34: Y=87%. Conversion=72%. $M_w$=3100 Da. $M_n$=1900 Da.

$^1$H-NMR: 3.98 (m, 0.7H), 3.47 (s, 0.17H), 3.27 (m, 0.7H), 2.88 (m, 0.7H), 2.56 (m, 1.8H), 2.16 (d, 2.2H), 1.91 (m, 1.4H), 1.80 (m, 2.1H), 1.54 (m, 6H), 1.14 (m, 2.2H), 1.07 (m, 1H), 0.94 (m, 2.2H), 0.58 (m, 2H), 0.07 (m, 3.9H); $^{13}$C-NMR: 206.5 (s), 140.0 (s), 131.4 (s), 53.1 (t), 39.8 (t), 38.1 (d), 37.3 (t), 35.8 (s), 34.1 (s), 33.7 (t), 33.5 (t), 30.7 (q), 28.4 (q), 27.9 (t), 23.2 (t), 22.4 (q), 19.3 (t), 17.3 (t), 16.8 (t), 16.6 (t), 1.9 (q), 1.3 (q), −0.3 (q), −1.0 (q).

Copolymer 39: Y=73%. Conversion=71%. $M_w$=6500 Da. $M_n$=3500 Da.

$^1$H-NMR: 3.97 (m, 0.7H), 3.46 (s, 0.1H), 3.26 (m, 0.7H), 2.87 (m, 0.7H), 2.54 (m, 1.9H), 2.16 (d, 2.2H), 2.07 (m, 0.4H), 1.91 (m, 1.6H), 1.80 (m, 2.2H), 1.54 (m, 3H), 1.49 (m, 1.3H), 1.41 (m, 1.6H), 1.14 (m, 2.2H), 1.07 (m, 1.3H), 0.94 (m, 2.2H), 0.59 (m, 2H), 0.07 (m, 4H); $^{13}$C-NMR: 206.5 (s), 140.0 (s), 131.4 (s), 53.1 (t), 39.8 (t), 38.2 (d), 37.4 (t), 35.8 (s), 33.7 (t), 30.7 (q), 28.4 (q), 27.9 (t), 23.2 (t), 22.4 (q), 19.3 (t), 17.3 (t), 16.9 (t), 16.6 (t), 1.3 (q), 0.8 (q), −0.3 (q), −0.7 (q).

Characterization of copolymers releasing 2-methyl-5-(prop-1-en-2-yl)cyclohex-2-enone or (−)carvone of formula P-3

Copolymer 11: Y=91%. Conversion=95%. $M_w$=17000 Da. $M_n$=4300 Da.

$^1$H-NMR: 4.79 (m, 1H), 4.76 (m, 1H), 2.85 (m, 1H), 2.60 (m, 1H), 2.51 (m, 2H), 2.48 (m, 1H), 2.33 (m, 3H), 1.79 (m, 1H), 1.75 (m, 3H), 1.61 (m, 2H), 1.22 (m, 2H), 1.14 (m, 1H), 0.64 (m, 2H), 0.09 (m, 3H); $^{13}$C-NMR: 209.6 (s), 146.8 (s), 111.0 (t), 50.2 (d), 46.2 (t), 44.4 (d), 40.4 (d), 39.6 (t), 34.1 (t), 23.6 (t), 20.6 (q), 17.3 (t), 12.8 (q), −0.14 (q).

Copolymer 12: Y=96%. Conversion=100%. $M_w$=35000 Da. $M_n$=11000 Da.

$^1$H-NMR: 4.79 (m, 1H), 4.76 (m, 1H), 2.85 (m, 1H), 2.60 (m, 1H), 2.51 (m, 2H), 2.48 (m, 1H), 2.33 (m, 3H), 1.79 (m, 1H), 1.75 (m, 3H), 1.61 (m, 2H), 1.22 (m, 2H), 1.14 (m, 1H), 0.64 (m, 2H), 0.09 (m, 3.6H); $^{13}$C-NMR: 209.8 (s), 146.6 (s), 110.5 (t), 50.2 (d), 46.4 (t), 44.4 (d), 40.4 (d), 39.6 (t), 34.2 (t), 23.5 (t), 20.4 (q), 17.3 (t), 12.7 (q), 1.4 (q), −0.2 (q).

Copolymer 13: Y=86%. Conversion=83%. $M_w$ (SEC)= 2100 Da. $M_n$=1500 Da.

$^1$H-NMR: 4.78 (m, 1.9H), 2.89 (m, 0.7H), 2.57 (m, 4H), 2.32 (m, 2H), 2.20 (m, 0.7H), 1.99 (m, 0.5H), 1.82 (m, 1H), 1.75 (m, 3H), 1.62 (m, 2H), 1.23 (m, 3H), 0.63 (m, 2H), 0.09 (m, 6H); $^{13}$C-NMR: 209.8 (s), 147.1 (s), 146.7 (s), 146.4 (s), 144.6 (d), 111.1 (t), 110.5 (t), 110.3 (t), 110.2 (t), 50.2 (d), 50.1 (d), 48.8 (d), 46.4 (t), 46.0 (t), 44.4 (d), 43.3 (t), 43.2 (t), 41.7 (t), 40.7 (d), 40.2 (d), 39.6 (t), 36.0 (t), 35.6 (t), 34.3 (t), 34.2 (t), 34.0 (t), 32.8 (t), 32.0 (t), 31.2 (t), 27.9 (t), 23.8 (t), 23.6 (t), 23.4 (t), 21.5 (d), 21.1 (q), 20.9 (q), 20.5 (q), 20.3 (q), 17.3 (t), 16.5 (t), 15.7 (q), 14.2 (q), 12.6 (q), 1.9 (q), 1.3 (q), −0.3 (q), −1.0 (q).

Copolymer 14: Y=98%. Conversion=100%. $M_w$=39000 Da. $M_n$=16000 Da.

$^1$H-NMR: 4.79 (m, 1H), 4.76 (m, 1H), 2.85 (m, 1H), 2.60 (m, 1H), 2.51 (m, 2H), 2.48 (m, 1H), 2.33 (m, 3H), 1.79 (m, 1H), 1.75 (m, 3H), 1.61 (m, 2H), 1.22 (m, 2H), 1.14 (m, 1H), 0.64 (m, 2H), 0.09 (m, 7H); $^{13}$C-NMR: 209.7 (s), 146.6 (s), 110.3 (t), 50.2 (d), 46.2 (t), 44.4 (d), 40.4 (d), 39.6 (t), 34.2 (t), 23.6 (t), 20.3 (q), 17.3 (t), 12.6 (q), 1.2 (q), −0.3 (q).

Copolymer 30: Y=80%. Conversion=92%. $M_w$=3600 Da. $M_n$=2060 Da.

$^1$H-NMR: 4.79 (m, 0.92H), 4.76 (m, 0.92H), 3.48 (s, 0.18H), 3.39 (s, 0.24H), 2.85 (m, 0.9H), 2.60 (m, 0.9H), 2.51 (m, 1.8H), 2.48 (m, 0.9H), 2.33 (m, 2.7H), 1.79 (m, 0.9H), 1.75 (m, 2.7H), 1.62 (m, 2H), 1.22 (m, 2H), 1.15 (m, 0.8H), 0.64 (m, 2H), 0.09 (m, 4.1H); $^{13}$C-NMR: 209.8 (s), 147.1 (s), 146.6 (s), 111.5 (t), 110.3 (t), 50.2 (d), 48.8 (d), 46.4 (t), 46.1 (t), 44.4 (d), 43.1 (t), 40.7 (d), 40.2 (t), 39.6 (t), 35.9 (t), 35.4 (t), 34.2 (t), 32.3 (t), 32.0 (t), 27.8 (t), 23.6 (t), 20.8 (q), 20.5 (q), 17.2 (t), 16.8 (t), 12.6 (q), 1.3 (q), −0.2 (q), −0.6 (q).

Characterization of copolymers releasing (E)-3,7-dimethylocta-2,6-dienal or citral of formula P-4

Copolymer 37: Y=90%. Conversion=81%. $M_w$=2300 Da. $M_n$=4100 Da.

$^1$H-NMR: 9.86 (m, 0.7H), 5.08 (m, 0.8H), 3.71 (m, 0.5H), 3.47 (s, 2.6H), 2.53 (m, 1H), 2.51 (m, 2H), 2.10 (m, 2H), 1.68 (m, 3H), 1.61 (m, 6H), 1.40 (m, 2H), 1.22 (m, 1.3H), 0.64 (m, 2H), 0.09 (m, 4H); $^{13}$C-NMR: 201.7 (d), 191.4 (d), 190.9 (d), 132.2 (s), 128.7 (d), 127.4 (d), 123.5 (d), 122.6 (t), 122.3 (d), 58.3 (t), 52.6 (t), 50.7 (q), 49.9 (q), 45.8 (s), 41.0 (t), 40.6 (t), 30.9 (t), 30.8 (t), 30.7 (t), 27.9 (t), 26.4 (q), 25.7 (q), 25.6 (q), 23.2 (t), 22.9 (t), 18.4 (q), 17.7 (q), 17.6 (t), 17.5 (t), 15.3 (t),1.2 (q), −0.4 (q), −3.1 (q).

Copolymer 38: Y=95%. Conversion=75%. $M_w$=4050 Da. $M_n$=2250 Da.

$^1$H-NMR: 9.86 (m, 0.75H), 5.08 (m, 1.2H), 3.73 (m, 0.3H), 3.47 (s, 0.7H), 2.58 (m, 0.5H), 2.53 (m, 1.6H), 2.51 (m, 1.6H), 2.22 (m, 1H), 2.17 (m, 0.7H), 2.10 (m, 1.8H), 1.98 (m, 0.5H), 1.68 (m, 3.8H), 1.61 (m, 7.2H), 1.40 (m, 2.5H), 1.21 (m, 0.7H), 0.64 (m, 2H), 0.10 (m, 7H); $^{13}$C-NMR: 201.6 (d), 163.8 (s), 132.2 (s), 123.5 (d), 52.6 (t), 45.8 (s), 41.0 (t), 40.6 (t), 30.9 (t), 30.8 (t), 30.7 (t), 27.1 (t), 26.4 (q), 25.7 (t), 25.6 (q), 25.1 (q), 23.2 (t), 22.9 (t), 17.7 (q), 17.6 (t), 15.3 (t), 1.1 (q), −0.4 (q), −0.9 (q), −1.5 (q), −3.1 (q).

Copolymer 40: Conversion=80%. $M_w$=4700 Da. $M_n$=2550 Da.

$^1$H-NMR: 9.86 (m, 0.8H), 5.08 (m, 1.4H), 3.47 (m, 0.7H), 2.52 (m, 3.3H), 2.22 (m, 1.5H), 2.17 (m, 0.9H), 2.10 (m, 1.8H), 1.68 (m, 4.6H), 1.61 (m, 8H), 1.40 (m, 2.6H), 0.64 (m, 2H), 0.11 (m, 3H); $^{13}$C-NMR: 201.6 (d), 132.2 (s), 123.5 (d), 52.6 (t), 45.8 (s), 41.0 (t), 30.9 (t), 30.7 (t), 26.4 (q), 25.7 (t), 25.6 (q), 23.2 (t), 22.9 (t), 17.7 (q), 17.6 (t), 15.3 (t), −0.3 (q), −3.0 (q).

Characterization of copolymers releasing 1-(5,5-Dimethylcyclohex-1-en-1-yl)pent-4-en-1-one of formula P-7

Copolymer 35: Conversion=85%. $M_w$=3100 Da. $M_n$=2100 Da.

$^1$H-NMR: 5.83 (m, 1H), 5.04 (m, 1H), 4.98 (m, 0.7H), 3.43 (s, 0.7H), 2.61 (m, 6H), 2.33 (m, 2.4H), 1.92 (m, 1H), 1.74 (m, 1H), 1.57 (m, 3H), 1.43 (m, 1.5H), 1.23 (m, 1.6H), 0.96 (m, 3H), 0.90 (m, 3H), 0.59 (m, 2.4H), 0.07 (m, 4.8H); $^{13}$C-NMR: 200.8 (s), 138.5 (d), 137.7 (d), 137.6 (d), 137.4 (d), 115.0 (t), 114.9 (d), 52.2 (d), 50.3 (d), 49.9 (d), 44.8 (d), 44.5 (d), 43.8 (t), 42.6 (t), 39.3 (t), 38.9 (t), 36.7 (t), 36.4 (t), 35.6 (t), 34.8 (t), 34.2 (t), 33.2 (t), 32.8 (q), 32.4 (q), 30.4 (t), 30.0 (t), 28.7 (s), 28.2 (t), 27.9 (t), 27.7 (t), 27.4 (t), 24.4 (q), 24.2 (q), 24.1 (t), 23.8 (t), 23.6 (t), 17.2 (t), 16.7 (t), 16.6 (t), 1.2 (q), −0.3 (q).

Characterization of copolymers releasing 1-(5-Ethyl-5-methylcyclohex-1-en-1-yl)pent-4-en-1-one of formula P-7

Copolymer 36: Y=76%. Conversion=90%. $M_w$=4800 Da. $M_n$=2900 Da.

$^1$H-NMR: 5.83 (m, 1H), 5.04 (m, 1H), 4.98 (m, 1H), 3.43 (s, 0.7H), 2.61 (m, 6H), 2.33 (m, 2H), 1.91 (m, 1H), 1.60 (m, 6H), 1.23 (m, 4H), 0.83 (m, 6H), 0.90 (m, 3H), 0.59 (m, 2.2H), 0.07 (m, 4.5H); $^{13}$C-NMR: 212.2 (s), 210.1 (s), 137.6 (d), 137.4 (d), 115.0 (t), 52.0 (d), 51.7 (d), 50.1 (d), 49.6 (d), 45.4 (d), 45.0 (d), 44.5 (d), 42.6 (t), 40.9 (t), 40.7 (t), 39.3 (t), 39.2 (t), 38.1 (t), 37.7 (t), 36.8 (t), 35.9 (t), 35.0 (t), 34.8 (t), 33.5 (t), 33.3 (t), 32.6 (s), 32.5 (s), 32.4 (s), 32.3 (s), 31.9 (t), 31.1 (t), 30.9 (t), 30.3 (t), 29.9 (t), 28.8 (q), 28.2 (q), 27.9 (t), 27.8 (t), 27.7 (t), 27.4 (t), 23.8 (t), 23.7 (t), 23.5 (t), 21.2 (q), 21.1 (q), 17.2 (t), 16.7 (t), 16.6 (t), 8.0 (q), 7.8 (q), 7.7 (q), 7.6 (q), 1.3 (q), 0.8 (q), −0.3 (q), −0.6 (q).

Preparation of copolymers of ({3-[(4-oxo-4-(2,6,6-trimethyl cyclohex-3-en-1-yl)butan-2-yl)thio]propyl}methyl)siloxane in N,N,N-triethanolamine (releasing (±)-trans-δ-damascone) (41)

In a 100 mL round-bottomed flask, 3-(dimethoxy(methyl) silyl)propane-1-thiol (527 mmol) was dissolved in water (475 mmol) in the presence of sodium hydroxide (12.06 mmol) to give an emulsion. Reaction mixture was stirred at r.t. for 15 h. An emulsion was obtained. Reaction mixture was diluted with ethyl acetate (150 mL), washed with of a aq. HCl 5 wt % (100 mL) and water (100 mL). The organic layer was dried with $MgSO_4$. Poly[(3-mercaptopropyl) methyl]siloxane was dried at 50° C. under vacuum (72.1 g of a colorless oil).

In a 100 mL round-bottomed flask poly[(3-mercaptopropyl)methyl]siloxane (37.4 mmol of repeating unit, $M_n$=1030 g/mol, $M_w$=1320 g/mol) was dissolved in (E)-1-(2,6,6-trimethylcyclohex-3-en-1-yl)but-2-en-1-one (δ-damascone, 31.0 mmol, 0.83 eq.) and triethanolamine (75 mmol) to give a translucent solution. The reaction mixture was stirred 15 h at room temperature and the product was used directly.

Copolymer 41: Conversion=96%.

$^1$H-NMR: 5.53 (m, 0.8H), 5.44 (m, 0.8H), 5.06 (m, 6.5H), 3.63 (m, 13H), 3.29 (m, 0.8H), 2.90 (m, 0.3H), 2.71 (m, 1.1H), 2.58 (m, 13H), 2.51 (m, 2.8H), 2.22 (m, 0.8H), 1.97 (m, 0.8H), 1.70 (m, 1.5H), 1.65 (m, 1.5H), 1.29 (m, 2.6H), 0.99 (m, 2.6H), 0.95 (m, 2.6H), 0.90 (m, 2.6H), 0.64 (m, 2H), 0.10 (m, 3H); $^{13}$C-NMR: 212.4 (s), 131.8 (d), 124.2 (d), 124.1 (d), 62.9 (d), 62.8 (d), 59.4 (t), 57.0 (t), 55.3 (t), 55.2 (t), 41.7 (t), 34.3 (t), 34.2 (d), 33.1 (s), 33.0 (s), 31.7 (d), 31.5 (d), 29.8 (q), 27.9 (t), 23.5 (t), 21.9 (q), 21.7 (q), 20.7 (q), 20.0 (q), 19.9 (q), 18.4 (s), 17.3 (t), 17.1 (t), 16.8 (t), 16.5 (t), −0.3 (q), −1.0 (q).

Comparative Example 1

Preparation of Copolymers According to the Prior Art

Preparation of poly(dimethylsiloxane), bis[methyl(3-((1-oxo-1-(2,6,6-trimethylcyclohex-3-en-1-yl)propan-2-yl) amino)propyl)dimethylsiloxane] terminated (Comparative copolymer 1: prepared by using the same starting materials as per Example 1 or 2 of US 2010/120657 but at room temperature to minimize the cross linking and being as close as possible to the present invention's polymers—Comparative copolymer 1 is not exemplified as such in US 2010/120657)

In a 50 mL round-bottomed flask were added poly(dimethylsiloxane), bis(3-aminopropyl) terminated (5.12 mL, 2.0 mmol $NH_2$ group) and (E)-1-(2,6,6-trimethylcyclohex-3-en-1-yl)but-2-en-1-one (0.77 g, 4.0 mmol) to give a colorless solution. DBU (0.03 mL, 0.2 mmol) was added and the reaction mixture was stirred 3 h at room temperature to afford a colorless oil.

Conversion=100%. $M_n$=2300 Da. $M_w$=4500 Da. Viscosity=0.1 Pa·s.

$^1$H-NMR: 5.44 (m, 1H), 5.38 (m, 1H), 3.40 (m, 8H), 3.06 (m, 0.8H), 2.63 (m, 0.5H), 2.53 (m, 2H), 2.44 (m, 2H), 2.16 (m, 1H), 1.88 (m, 1H), 1.62 (m, 1.5H), 1.48 (m, 2H), 1.27 (m, 0.8H), 0.99 (m, 3H), 0.88 (m, 3H), 0.81 (m, 3H), 0.52 (m, 2H), 0.01 (m, 110H); $^{13}$C-NMR: 214.4 (s), 131.9 (d), 124.2 (d), 124.1 (d), 63.0 (d), 55.0 (t), 50.6 (q), 50.2 (t), 49.7 (q), 48.7 (d), 48.6 (d), 41.8 (t), 33.1 (s), 33.0 (s), 31.6 (d), 31.5 (d), 29.9 (q), 29.8 (q), 23.9 (t), 23.7 (t), 20.7 (q), 20.4 (q), 20.0 (q), 19.9 (q), 10.3 (s), 1.3 (q), 1.0 (q), 0.9 (q), −1.6 (q), −1.7 (q), −9.2 (q).

Preparation of copolymer poly(dimethylsiloxane), bis [methyl(3-((1-oxo-1-(2,6,6-trimethylcyclohex-3-en-1-yl) propan-2-yl)amino)propyl)dimethoxysiloxane] terminated (Comparative copolymer 2: prepared according to Example 1 of US 2010/120657)

In a 50 mL round-bottomed flask poly(dimethylsiloxane), hydroxy terminated (4.00 g, 1.6 mmol, origin Aldrich) and 3-(trimethoxysilyl)propan-1-amine (0.61 g, 3.3 mmol) were mixed together to give a colorless solution. The reaction mixture was stirred 4 h at 125° C. to form a gel. Comparative copolymer 2 was not dispersible in aqueous perfuming consumer products.

Preparation of copolymer poly(dimethylsiloxane), bis [methyl(3-((1-oxo-1-(2,6,6-trimethylcyclohex-3-en-1-yl) propan-2-yl)amino)propyl)dimethoxysiloxane] terminated (Comparative copolymer 3: thio derivative of formula (I) reacted with co-monomer according to prior art US 2010/120657)

In a 100 mL round-bottomed flask, (3-mercaptopropyl) (methyl)dimethoxysilane (5.00 g, 26.3 mmol), (dimethyl) diethoxysilane (0.81 g, 5.3 mmol), and (methyl)triethoxysilane (0.06 g, 0.3 mmol) were stirred with water (1.06 g, 58.7 mmol) to give a colorless solution. Reaction mixture was stirred at 60° C. for 20 h. Then, (E)-1-(2,6,6-trimethylcyclohex-3-en-1-yl)but-2-en-1-one (5.09 g, 26.5 mmol) was stirred for 3 h at room temperature. A precipitate was observed. Comparative copolymer 3 was not dispersible in aqueous perfuming consumer products.

Preparation of copolymer poly(dimethylsiloxane), bis [methyl(3-((1-oxo-1-(2,6,6-trimethylcyclohex-3-en-1-yl) propan-2-yl)amino)propyl)dimethoxysiloxane] terminated (Comparative copolymer 4: thio derivative of formula (I) reacted with co-monomer according to prior art US 2010/120657)

In a 100 mL round-bottomed flask was (3-mercaptopropyl)(methyl)dimethoxysilane (4.55 g, 24.0 mmol), (dimethyl)diethoxysilane (0.75 g, 4.9 mmol), and (methyl)triethoxy silane (0.58 g, 3.2 mmol) in water (1.01 g, 55.9 mmol) to give a colorless solution. Reaction mixture was stirred at 60° C. for 15 h. Then, (E)-1-(2,6,6-trimethylcyclohex-3-en-1-yl)but-2-en-1-one (4.61 g, 24.0 mmol) was added and the reaction mixture was stirred at r.t. for additional 3 h. A precipitate was observed. Comparative copolymer 4 was not dispersible in aqueous perfuming consumer products.

As further reference compounds, we compared the performance of the invention's copolymers of formula (I) to the prior art 3-(dodecylthio)-1-(2,6,6-trimethyl-3-cyclohexen-1-yl)-1-butanone monomer described as Example 4a in WO 03/049666 and referred to as "Prior art (WO 03/049666)" and to the prior-art poly(methoxyethylene-alt-maleic acid mono-{2-[1-methyl-3-oxo-3-(2,6,6-trimethyl-cyclohex-3-enyl)-propylsulfanyl]-ethyl}ester) described as Example 4 in WO 2008/044178 and referred to as "Prior art (WO 2008/044178)".

Example 2

Evaluation of the Release of a Perfuming Ingredient from the Invention's Copolymers Incorporated into a Consumer Product (Fabric Softener)

The liberation of an α,β-unsaturated ketone from the present invention's copolymers of formula (I) was tested in a fabric softening application using a fabric softener with the following final composition:

| | |
|---|---|
| Stepantex ® VL90 A (origin: Stepan) | 16.5% by weight |
| Calcium chloride (10% aq. solution) | 0.6% by weight |
| Water | 82.9% by weight |

The different copolymers prepared in Example 1 were individually dispersed in the above described fabric softener (5.40 g) at a concentration to release a total amount of 0.135 mmol of the fragrance. Then ethanol or THF (3 mL) were added to the mixture. The samples were shaken and left standing overnight.

In a beaker, the fabric softening surfactant emulsion containing the compound of formula (I) (2.60 g) was diluted with demineralised cold tap water (600 g) and one cotton sheet (EMPA cotton test cloth Nr. 221, origin: Eidgenössische Materialprüfanstalt (EMPA), pre-washed with an unperfumed detergent powder and cut to ca. 12×12 cm sheets) was added to each beaker. The sheet was manually stirred for 3 min, left standing for 2 min, then wrung out by hand and line-dried for 1 or 3 days. As a reference sample, a solution containing an equimolar amount of unmodified $\alpha,\beta$-unsaturated ketone to be liberated from the copolymers of formula (I) was added to another sample of the fabric softening surfactant emulsion and was treated as described above. All measurements were performed at least twice.

One dry cotton sheet was put into a headspace sampling cell (internal volume ca. 160 mL), thermostatted at 25° C. and exposed to a constant air flow (200 mL/min), respectively. The air was filtered through active charcoal and aspirated through a saturated solution of NaCl, corresponding to a constant humidity of ca. 75%. During 15 min, the volatiles were adsorbed onto a waste Tenax® cartridge, then during 15 min onto a clean Tenax® cartridge. The sampling was repeated 7 times every 60 min (45 min trapping on the waste cartridge and 15 min on a clean cartridge); the waste cartridges were discarded. The cartridges with the volatiles were thermally desorbed on a Perkin Elmer TurboMatrix ATD desorber coupled to an Agilent Technologies 7890A GC System equipped with a HP-1 capillary column (30 m, i.d. 0.32 mm, film 0.25 µm) and a FID detector. The volatiles were analyzed using a temperature gradient from 60° C. to 200° C. at 15° C./min. Headspace concentrations (in ng/L of air) were obtained by external standard calibration with different concentrations of the $\alpha,\beta$-unsaturated ketone to be liberated. The headspace concentrations measured after 150 min of sampling above the dry cotton sheets are listed in Tables 2 and 3 and compared to the headspace concentrations of the corresponding unmodified $\alpha,\beta$-unsaturated ketone to be released from the compounds of formula (I) used as the reference.

TABLE 2

Average headspace concentrations of $\alpha,\beta$-unsaturated ketones released from copolymers of formula (I) as prepared in Example 1 and of the corresponding unmodified $\alpha,\beta$-unsaturated ketone (reference) in a fabric softener application after drying for 1 day and sampling for 150 min.

| Compound | Amount of $\alpha,\beta$-unsaturated ketone released [ng/L] | Factor of increase with respect to the reference |
|---|---|---|
| Copolymer 3 | 31.1 | 11 |
| Copolymer 7 | 39.0 | 14 |
| Copolymer 15 | 58.8 | 22 |
| Copolymer 16 | 94.5 | 35 |
| Copolymer 17 | 84.8 | 31 |

TABLE 2-continued

Average headspace concentrations of $\alpha,\beta$-unsaturated ketones released from copolymers of formula (I) as prepared in Example 1 and of the corresponding unmodified $\alpha,\beta$-unsaturated ketone (reference) in a fabric softener application after drying for 1 day and sampling for 150 min.

| Compound | Amount of $\alpha,\beta$-unsaturated ketone released [ng/L] | Factor of increase with respect to the reference |
|---|---|---|
| Copolymer 22 | 88.5 | 33 |
| Copolymer 23 | 35.2 | 13 |
| Copolymer 27 | 106.6 | 39 |
| Copolymer 28 | 35.0 | 13 |
| Copolymer 29 | 37.4 | 14 |
| Prior art (WO 03/049666) | 34.7 | 13 |
| δ-damascone (reference) | 2.7 | 1 |

TABLE 3

Average headspace concentrations of $\alpha,\beta$-unsaturated ketones released from copolymers of formula (I) as prepared in Example 1 and of the corresponding unmodified $\alpha,\beta$-unsaturated ketone (reference) in a fabric softener application after drying for 3 days and sampling for 150 min.

| Compound | Amount of $\alpha,\beta$-unsaturated ketone released [ng/L] | Factor of increase with respect to the reference |
|---|---|---|
| Copolymer 1 | 42.5 | 35 |
| Copolymer 2 | 35.1 | 29 |
| Copolymer 4 | 77.7 | 65 |
| Copolymer 8 | 26.7 | 22 |
| Copolymer 9 | 22.2 | 19 |
| Copolymer 10 | 69.0 | 58 |
| Copolymer 15 | 43.3 | 36 |
| Copolymer 16 | 54.3 | 45 |
| δ-damascone (reference) | 1.2 | 1 |

Example 3

Evaluation of the Release of a Perfuming Ingredient from the Invention's Copolymers Incorporated into a Consumer Product (Detergent Powder)

A non-perfumed, commercially available powder detergent (Via Professional Sensitive, origin: Unilever, 1.8 g), a solution of one of the invention's copolymers of formula (I) in ethanol (0.2 mL) or ethanol/water (1:1, 0.4 mL) at a concentration to release a total amount of 0.3 mmol of the fragrance, 400 mL of tap water and one cotton sheet (see Example 2) were added to a stainless steel container of a Linitest® washing machine (origin: Heraeus). Similarly, a reference sample containing the unmodified $\alpha,\beta$-unsaturated ketone to be released (0.3 mmol) instead of the invention's copolymer of formula (I) was prepared in the same way in a second stainless steel container. The containers were fixed inside the Linitest® machine and rotated at 45° C. for 20 min. The cotton sheets were then rinsed twice by agitating them manually in 600 mL of tap water for 2 min, and line-dried overnight. The sheets were analyzed the next day, as described in Example 2. The headspace system was equilibrated during 120 min by pumping air through a waste Tenax® cartridge. Then the volatiles were adsorbed during 30 min onto a clean Tenax® cartridge. The cartridges used for the equilibration were discarded, the other cartridges desorbed and analyzed as described in Example 2. All measurements were performed at least twice.

The headspace concentrations measured after 150 min of sampling above the dry cotton sheets are listed in Table 4 and compared to the headspace concentrations of the corresponding unmodified α,β-unsaturated ketone to be released from the copolymers of formula (I) used as the reference.

TABLE 4

Average headspace concentrations of α,β-unsaturated ketones released from copolymers of formula (I) as prepared in Example 1 and of the corresponding unmodified α,β-unsaturated ketone (reference) in a powder detergent application after drying for 1 day and sampling for 150 min.

| Compound from | Amount of α,β-unsaturated ketone released [ng/l] | Amount of unmodified α,β-unsaturated ketone (reference) [ng/l] | Factor of increase with respect to the reference |
|---|---|---|---|
| Copolymer 18 | 14.8 | 1.8 | 8 |
| Copolymer 19 | 9.0 | 1.8 | 5 |
| Copolymer 20 | 5.5 | 1.8 | 3 |
| Copolymer 21 | 9.5 | 1.8 | 5 |

Example 4

Olfactive Evaluation of the Release of a Perfuming Ingredient from the Invention's Copolymers Incorporated into a Consumer Product (Liquid Detergent)

The tests were carried out using a standard liquid detergent base. The washing of the cotton terry towels was carried out with 75 g of an un-perfumed detergent base (universal kraft gel, origin: Henkel, Germany) to which were previously added the pure α,β-unsaturated ketone or aldehyde (δ-damascone, 0.05%) as the reference or, alternatively, the corresponding molar amount of δ-damascone releasing copolymers 1-41 prepared in Example 1. In a first test copolymers 2, 3 and 5 with different $M_w$ were evaluated and compared to copolymers 6, 22, 24, 26 and 27, all of which having a relatively low $M_w$. A washing machine (Miele Novotronic W300-33CH) was loaded with 10 small terry towels (18 cm×18 cm, about 30 g each) and 6 large cotton towels for a total wash load of 2 kg. The load was washed at 40° C. using a short cycle program and rinsed twice at 900 rpm.

At the end of the washing, the 10 small terry towels were line-dried for 24 h and wrapped into aluminum foil for storage, before being evaluated for their olfactive intensity by 20 panelists after 3 and 7 days, using a scale ranging from "1" (no odor) to "7" (very strong odor). The following average odor intensities were determined for the different samples (Table 5).

TABLE 5

| Tested molecule | $M_w$ (Da) | Viscosity (Pa · s) | Evaluation after 3 d on cotton | Evaluation after 7 d on cotton | Ratio Invention/Prior art WO 03/049666 3 d | 7 d |
|---|---|---|---|---|---|---|
| δ-damascone (reference) | 192[a] | n.m. | 1.6 | 1.8 | n.a. | n.a. |
| Prior art (WO 03/049666) | 394[a] | 0.04 | 2.7 | 2.6 | n.a. | n.a. |
| Prior art (WO 2008/044178) | 160000[b] | solid | 2.4 | 2.3 | n.a. | n.a. |
| Comparative copolymer 1 | 4500[b] | 0.1 | 2.6 | 2.7 | 0.9 | 1.0 |
| Copolymer 2 | 6500[b] | 23.5 | 3.0 | 3.1 | 1.1 | 1.2 |
| Copolymer 3 | 3900[b] | 1.6 | 4.4 | 4.3 | 1.7 | 1.7 |
| Copolymer 5 | 18000[b] | 15.6 | 2.2 | 2.1 | 0.8 | 0.8 |
| Copolymer 6 | 3200[b] | 12.8 | n.m. | 3.2 | n.a. | 1.2 |
| Copolymer 22 | 3900[b] | 10.8 | n.m. | 3.2 | n.a. | 1.2 |
| Copolymer 23 | 6200[b] | 60 | 3.1 | 3.3 | 1.1 | 1.3 |
| Copolymer 24 | 3000[b] | 3.6 | n.m. | 3 | n.a. | 1.2 |
| Copolymer 26 | 3000[b] | 1.2 | n.m. | 3 | n.a. | 1.2 |
| Copolymer 27 | 4800[b] | 2.2 | n.m. | 2.9 | n.a. | 1.1 | n.a. = not applicable;

n.m. = not measured;

[a]molecular weight;

[b]weight average molecular weight.

The evaluation showed significant differences in intensity for the comparison of the samples (0.5 units of difference provide ≥95% of statistic significance, and 0.4 points difference represent 90% of statistic significance). The towels containing the copolymers according to the invention smelled stronger than the reference pure α,β-unsaturated ketone or aldehyde (δ-damascone). We also observed that in formulations with a high anionic/nonionic surfactant content submitted to a multi-rinse wash process, the $M_w$ of the copolymer influences the performance, with the lower $M_w$ copolymers performing better that their analogues with higher M. While the highest $M_w$ copolymer (5) with a $M_w$ of 18000 is performing at parity with the polymeric reference Prior art (WO 2008/044178), the copolymer 2 with a $M_w$ 6500 is performing significantly better than the polymeric reference Prior art (WO 2008/044178) on fabric dried for 3 and 7 days, and significantly better than the monomeric Prior art (WO 03/049666) on fabric dried for 3 and 7 days. Copolymer 3, with a low $M_w$ of 3900, is clearly outperforming both references Prior art (WO 03/049666) and Prior art (WO 2008/044178). It is also performing better than both copolymers 2 and 5 of the invention. Similarly, copolymers 6, 22, 24, 26 and 27 with low $M_w$ all performed better than the prior art compounds.

The same washing process as described above was applied to copolymers 15-17, prepared with N,N-dimethylaminopropylmethyl siloxane as comonomer, and their cationic analogues 18-21, to give the data summarized in Table 6.

TABLE 6

| Tested molecule | Viscosity (Pa · s) | Evaluation after 3 d on cotton | Evaluation after 7 d on cotton | Ratio Invention/Prior art WO 03/049666 | |
|---|---|---|---|---|---|
| | | | | 3 d | 7 d |
| δ-damascone (reference) | n.m. | 1.6 | 1.8 | n.a. | n.a. |
| Prior art (WO 03/049666) | 0.04 | 2.7 | 2.6 | n.a. | n.a. |
| Prior art (WO 2008/044178) | solid | 2.4 | 2.3 | 0.9 | 0.9 |
| Copolymer 15 | 9.3 | 3.2 | 2.8 | 1.2 | 1.1 |
| Copolymer 16 | 6.1 | 3.2 | 2.7 | 1.2 | 1.0 |
| Copolymer 17 | 2.4 | 2.9 | 2.7 | 1.1 | 1.0 |
| Copolymer 18 | n.m. | 2.5 | 3.1 | 0.9 | 1.2 |
| Copolymer 19 | n.m. | 2.5 | 2.5 | 0.9 | 1.0 |
| Copolymer 21 | n.m. | 2.9 | 2.9 | 1.1 | 1.1 |

All the invention's copolymers performed better than the pure α,β-unsaturated ketone or aldehyde (reference) (0.5 units of difference provide ≥95% of statistic significance). Furthermore, all the invention's polymers performed as good as, or even better than the polymeric reference Prior art (WO 2008/044178). The invention's polymers (15-17 and 21) are even performing better than the commercial monomeric reference Prior art (WO 03/049666).

The same test was performed on polyester sheets using three of the best performing low $M_w$ copolymers previously identified on cotton. Their performance was compared with the commercial reference Prior art (WO 03/049666). The results are reported in Table 7.

TABLE 7

| Tested molecule | Viscosity (Pa · s) | Evaluation after 3 days on polyester | Evaluation after 7 days on polyester | Ratio Invention/Prior art WO 03/049666 | |
|---|---|---|---|---|---|
| | | | | 3 d | 7 d |
| δ-damascone (reference) | n.m. | 1.6 | 1.5 | n.a. | n.a. |
| Prior art (WO 03/049666) | 0.04 | 2.2 | 2.2 | n.a. | n.a. |
| Comparative copolymer 1 | 0.1 | 2.5 | 2.8 | 1.1 | 1.3 |
| Copolymer 2 | 23.5 | 3.0 | 2.8 | 1.4 | 1.3 |
| Copolymer 3 | 1.6 | 3.6 | 4.0 | 1.6 | 1.8 |
| Copolymer 6 | 12.8 | 4.1 | 3.6 | 1.9 | 1.6 |
| Copolymer 22 | 10.8 | 4.9 | 4.9 | 2.2 | 2.2 |
| Copolymer 23 | 60 | 4.2 | 4.2 | 1.9 | 1.9 |
| Copolymer 24 | 3.6 | 4.2 | 4.0 | 1.9 | 1.8 |
| Copolymer 25 | 5.7 | 4.0 | 3.6 | 1.8 | 1.6 |

The evaluation showed significant differences in intensity for the comparison of the two samples (0.5 unit of difference provide ≥95% of statistic significance). The polyester sheets washed in the presence of the copolymers according to the invention smelled stronger and fresher than the pure reference α,β-unsaturated ketone (δ-damascone). Copolymers 2, 3, 6 and 22-25 were performing better than the commercial monomeric reference Prior art (WO 03/049666), and in particular copolymers 2, 3, 6 and 22-25 performed better than the Comparative copolymer 1.

The same test was performed with copolymer 13 (with low $M_w$, equivalent to 3 but releasing carvone instead of δ-damascone) on polyester sheets using pure carvone as the reference α,β-unsaturated ketone. The results are reported in Table 8.

TABLE 8

| Tested molecule | Viscosity (Pa · s) | Evaluation after 3 d on polyester | Evaluation after 7 d on polyester | Performance ratio | |
|---|---|---|---|---|---|
| | | | | 3 d | 7 d |
| Carvone | <0.1 | 2.2 | 1.9 | n.a. | n.a. |
| Copolymer 13 | 1.6 | 3.9 | 3.9 | 1.8 | 2.1 |

The evaluation showed significant differences in intensity for the comparison of the two samples (0.5 units of difference provide ≥95% of statistic significance). The polyester sheets washed in the presence of copolymer 13 according to the invention smelled much stronger and fresher than the reference α,β-unsaturated ketone (carvone).

The same test was performed with copolymer 13 on cotton (instead of polyester) sheets using carvone as the reference α,β-unsaturated ketone, the results are reported in Table 9.

TABLE 9

| Tested molecule | Evaluation after 3 d on cotton | Evaluation after 7 d on cotton | Performance ratio | |
|---|---|---|---|---|
| | | | 3 d | 7 d |
| Carvone | 2.2 | 2.0 | 1.0 | 1.0 |
| Copolymer 13 | 3.5 | 3.7 | 1.6 | 1.9 |

The evaluation showed significant differences in intensity for the comparison of the two samples (0.5 units of difference provide ≥95% of statistic significance). The cotton sheets containing copolymer 13 according to the invention smelled much stronger and fresher than the reference α,β-unsaturated ketone.

Example 5

Olfactive Evaluation of the Release of a Perfuming Ingredient from the Invention's Copolymers Incorporated into a Consumer Product (Powder Detergent)

The tests were carried out using a standard powder detergent base. The washing of the cotton terry towels was carried out with 75 g of an un-perfumed detergent base (a standard commercial base containing sodium percarbonate, benzenesulfonic acid, C10-13-alkyl derivs. sodium salts, sodium carbonate, sulfuric acid, mono C12-18 alkyl ester sodium salts, ethoxylated alcohols) to which were previously added pure δ-damascone (0.05%) as the α,β-unsaturated ketone or, alternatively, the corresponding molar amount of δ-damascone releasing copolymers 1-41 prepared in Example 1.

As a further reference, we compared the performance of the invention's copolymers of formula (I) to the Prior art (WO 03/049666), which was prepared and treated in the same way as described above.

A washing machine (Miele Novotronic W300-33CH) was loaded with 10 small terry towels (18 cm×18 cm, about 30 g each) and 6 large cotton towels for a total wash load of 2 kg. The load was washed at 40° C. using a short cycle program and rinsed twice at 900 rpm.

At the end of the washing, the 10 small terry towels were line-dried for 24 h and wrapped into aluminum foil for storage, before being evaluated for their olfactive intensity by 20 panelists after 3 and 7 days, using a scale ranging from "1" (no odor) to "7" (very strong odor). The following average intensities were determined for the different samples (Table 10).

TABLE 10

| Tested molecule | $M_w$ (Da) | Viscosity (Pa·s) | Evaluation after 3 d on cotton | Evaluation after 7 d on cotton | Ratio Invention/ Prior art WO 03/049666 | |
|---|---|---|---|---|---|---|
| | | | | | 3 d | 7 d |
| δ-damascone (reference) | 192[a] | n.m. | 1.6 | 1.8 | n.a. | n.a. |
| Prior art (WO 03/049666) | 394[a] | 0.04 | 2.7 | 3 | n.a. | n.a. |
| Copolymer 3 | 3900[b] | 1.6 | 3.5 | 4.5 | 1.3 | 1.5 |
| Copolymer 6 | 3200[b] | 12.8 | 2.9 | 3.9 | 1.1 | 1.3 | n.a. = not applicable;
n.m. = not measured;
[a]molecular weight;
[b]weight average molecular weight.

All the invention's polymers performed significantly better than the pure α,β-unsaturated ketone (reference) (0.5 units of difference provide ≥95% of statistic significance). The invention's copolymers 3 and 6 are even performing better than the monomeric Prior art (WO 03/049666).

The same test was performed using polyester instead of cotton sheets, the results are reported in Table 11.

TABLE 11

| Tested molecule | Evaluation after 3 d on polyester | Evaluation after 7 d on polyester | Ratio Invention/ Prior art WO 03/049666 | |
|---|---|---|---|---|
| | | | 3 d | 7 d |
| δ-damascone (reference) | 1.6 | 1.5 | n.a. | n.a. |
| Prior art (WO 03/049666) | 2.1 | 2.3 | n.a. | n.a. |
| Copolymer 3 | 3.8 | 4.4 | 1.8 | 1.9 |
| Copolymer 6 | 3.5 | 4.2 | 1.7 | 1.8 | n.a. = not applicable.

The polyester sheets washed in the presence of copolymers 3 and 6 according to the invention smelled stronger than the reference α,β-unsaturated ketone (δ-damascone) and even stronger than the monomeric Prior art (WO 03/049666).

Example 6

Olfactive Evaluation of the Release of a Perfuming Ingredient from the Invention's Copolymers Incorporated into a Consumer Product (Liquid Detergent Unit Dose Capsule—Single Chamber)

The tests were carried out using a standard unit dose liquid detergent base. The washing of the cotton terry towels was carried out with 35 g of a-unit dose base (a standard commercial base containing MEA-dodecylbenzesulfonate, MEA-hydrogenated cocoate, propylene glycol, C12-15 Pareth-7, water, glycerin, polyvinyl alcohol, perfume, pentasodium ethylenediamine tetramethylene phosphonate, ethanolamine, sorbitol, MEA-sulfate, PVP, subtilisin, glycol, butylphenyl methypropional, starch, hexyl cinnamal, boronic acid, 4-formylphenal, limonene, linalool, disodium distyrylbiphenyl disulfonate, alpha-isomethyl ionone, talc, amylase, Polymeric Blue colorant, sodium chloride, mannamase, Polymeric Yellow colorant) to which were previously added pure δ-damascone (0.05%) as α,β-unsaturated ketone or, alternatively, the corresponding molar amount of δ-damascone releasing copolymers prepared in Example 1.

As a further reference, we compared the performance of the invention's copolymers of formula (I) to the Prior art (WO 03/049666), which was prepared and treated in the same way as described above.

A washing machine (Miele Novotronic W300-33CH) was loaded with polyester sheets for a total wash load of 2 kg. The load was washed at 40° C. using a short cycle program and rinsed twice at 900 rpm. The data are summarized in Table 12.

TABLE 12

| Tested molecule | Evaluation after 3 d on polyester | Evaluation after 7 d on polyester | Ratio Invention/Prior art WO 03/049666 | |
|---|---|---|---|---|
| | | | 3 d | 7 d |
| δ-damascone (reference) | 1.7 | 1.9 | n.a. | n.a. |
| Prior art (WO 03/049666) | 2.7 | 2.5 | n.a. | n.a. |
| Copolymer 3 | 4 | 3.7 | 1.5 | 1.5 |
| Copolymer 6 | 3.6 | 3.7 | 1.3 | 1.5 | n.a. = not applicable.

The polyester sheets washed in the presence of copolymers 3 or 6 according to the invention smelled stronger than the free α,β-unsaturated ketone (δ-damascone) and even stronger than the monomeric Prior art (WO 03/049666).

Example 7

Olfactive Evaluation of the Release of a Perfuming Ingredient from the Invention's Copolymers Incorporated into a Consumer Product (Liquid Detergent Unit Dose Capsule—Dual Chamber)

The tests were carried out using a standard unit dose liquid detergent base with dual compartment. The washing of the cotton terry towels was carried out with 37 g of a unit dose base (a standard commercial base containing less than 5% phosphonates, between 15 and 30% anionic surfactant, non-ionic surfactant, soap, enzyme, optical brighteners, perfume, limonene, hexyl cinnamal, butylphenyl methylpropional) to which were previously added pure δ-damascone (0.05%) as α,β-unsaturated ketone or, alternatively, the corresponding molar amount of δ-damascone releasing copolymers 1-41 prepared in Example 1.

As a further reference, we compared the performance of the invention's copolymers of formula (I) to the Prior art (WO 03/049666), which was prepared and treated in the same way as described above.

A washing machine (Miele Novotronic W300-33CH) was loaded with 10 small terry towels (18 cm×18 cm, about 30 g each) and 6 large cotton towels for a total wash load of 2 kg. The load was washed at 40° C. using a short cycle program and rinsed twice at 900 rpm.

At the end of the washing, the 10 small terry towels were line-dried for 24 h and wrapped into aluminum foil for storage, before being evaluated for their olfactive intensity by 20 panelists after 3 and 7 days, using a scale ranging from "1" (no odor) to "7" (very strong odor). The following average intensities were determined for the different samples (Table 13).

TABLE 13

| Tested molecule | $M_w$ (Da) | Evaluation after 3 d on cotton | Evaluation after 7 d on cotton | Ratio Invention/Prior art WO 03/049666 | |
|---|---|---|---|---|---|
| | | | | 3 d | 7 d |
| Prior art (WO 03/049666) | 394[a] | 3.4 | 2.8 | n.a. | n.a. |
| Copolymer 3 | 3900[b] | 3.5 | 3.1 | 1.0 | 1.1 |
| Copolymer 6 | 3200[b] | 4.0 | 3.1 | 1.2 | 1.1 | n.a. = not applicable;
[a] molecular weight;
[b] weight average molecular weight.

All the invention's polymers performed significantly better than the monomeric Prior art (WO 03/049666) (0.5 units of difference provide ≥95% of statistic significance).

The same test was performed using polyester instead of cotton sheets, the results are reported in Table 14.

TABLE 14

| Tested molecule | Evaluation after 3 d on polyester | Evaluation after 7 d on polyester | Ratio Invention/Prior art WO 03/049666 | |
|---|---|---|---|---|
| | | | 3 d | 7 d |
| Prior art (WO 03/049666) | 3.4 | 2.9 | n.a. | n.a. |
| Copolymer 3 | 3.8 | 3.9 | 1.1 | 1.3 |
| Copolymer 6 | 4.5 | 4.4 | 1.3 | 1.5 | n.a. = not applicable.

The polyester sheets washed in the presence of copolymers 3 or 6 according to the invention smelled stronger than the monomeric Prior art (WO 03/049666).

Example 8

Olfactive Evaluation of the Release of a Perfuming Ingredient from the Invention's Copolymers Incorporated into a Consumer Product (Liquid Detergent Unit Dose Capsule—Triple Chamber)

The tests were carried out using a standard unit dose liquid detergent base with a dual compartment. The washing of the cotton terry towels was carried out with 37 g of a unit dose base (a standard commercial base consisting of MEA-dodecylbenzenesulfonate, propylene glycol, C12-14 Pareth-7, MEA-laureth sulfate, water, PEI ethoxylate, glycerin, perfume, co-polymer of PEG/vinyl acetate, dodecylbenzene sulfonic acid, potassium sulfite, magnesium chloride, PEG/PPG-10/2 propylheptyl ether, benzyl salicylate, hydrogenated castor oil, ethanolamine, polystyrene, hexyl cinnamal, citronellol, butylphenyl methylpropional, sodium formate, sorbitol, protease, linalool, coumarin, tripropylene glycol, 2-propenoic acid, polymer with ethenylbenzene, disodium distyrylbiphenyl disulfonate, geraniol, sulfuric acid, glycosidase, sodium acetate, cellulase, colorant, sodium lauryl sulfate, sodium sulfat E, sodium polynaphthalenesulfonate) to which were previously added pure δ-damascone (0.05%) as α,β-unsaturated ketone or, alternatively, the corresponding molar amount of δ-damascone releasing copolymers prepared in Example 1.

As a further reference, we compared the performance of the invention's copolymers of formula (I) to the Prior art (WO 03/049666), which was prepared and treated in the same way as described above.

A washing machine (Miele Novotronic W300-33CH) was loaded with polyester sheets for a total wash load of 2 kg. The load was washed at 40° C. using a short cycle program and rinsed twice at 900 rpm.

TABLE 15

| Tested molecule | Evaluation after 3 days on polyester | Evaluation after 7 days on polyester | Ratio Invention/Prior art WO 03/049666 | |
|---|---|---|---|---|
| | | | 3 d | 7 d |
| Prior art (WO 03/049666) | 4.0 | 4.0 | n.a. | n.a. |
| Copolymer 3 | 4.4 | 4.1 | 1.1 | 1.0 |
| Copolymer 6 | 4.9 | 4.7 | 1.2 | 1.2 | n.a. = not applicable.

The polyester sheets washed in the presence of copolymers 3 or 6 according to the invention smelled stronger than the monomeric Prior art (WO 03/049666).

Example 9

Olfactive Evaluation of the Release of Various Perfuming Ingredient from the Invention's Copolymers Incorporated into a Consumer Product (Liquid Detergent)

Various copolymers of low $M_w$, equivalent to copolymer 6, but releasing different α,β-unsaturated ketones other than δ-damascone, such as damascenone, carvone or Neobutenone®, were assessed.

The tests were carried out using a standard liquid detergent base. The washing of the cotton terry towels was carried out with 75 g of an un-perfumed detergent base to which were previously added the corresponding molar amount to deliver 0.05% of α,β-unsaturated ketone.

A washing machine (Miele Novotronic W300-33CH) was loaded with 10 small terry towels (18 cm×18 cm, about 30 g each), and 6 large cotton towels for a total wash load of 2 kg. The load was washed at 40° C. using a short cycle program and rinsed twice at 900 rpm.

At the end of the washing, the 10 small terry towels were line-dried for 24 h and wrapped into aluminum foil for storage, before being evaluated for their olfactive intensity by 20 panelists after 4 and 7 days, using a scale ranging from "1" (no odor) to "7" (very strong odor). The following average intensities were determined for the different samples (Table 16).

TABLE 16

| Tested molecule | $M_w$ (Da) | Viscosity (Pa · s) | Evaluation after 4 d on cotton | Evaluation after 7 d on cotton | Ratio Invention/ Prior art WO 03/049666 3 d | 7 d |
|---|---|---|---|---|---|---|
| Prior art (WO 03/049666) | 394[a] | 0.04 | 2.1 | 2.3 | n.a. | n.a. |
| Copolymer 6 | 3200[b] | 12.1 | 2.7 | 3.6 | 1.3 | 1.6 |
| Copolymer 32 | 4300[b] | 8.2 | 3.1 | 3.4 | 1.5 | 1.5 |
| Copolymer 33 | 2900[b] | 5.1 | 3.2 | 3.3 | 1.5 | 1.4 |
| Copolymer 30 | 3600[b] | 19.1 | 3.1 | 3.6 | 1.5 | 1.6 |
| Copolymer 35 | 3100[b] | 5.1 | 4.8 | 5.1 | 2.3 | 2.2 |

[a]molecular weight;
[b]weight average molecular weight.

All the invention's polymers performed significantly better than the monomeric Prior art (WO 03/049666).

The same test was performed using polyester instead of cotton sheets and after line-drying for 3 and 7 days, the results are reported in Table 17.

TABLE 17

| Tested molecule | Viscosity (Pa · s) | Evaluation after 3 d on polyester | Evaluation after 7 d on polyester | Ratio Invention/ Prior art WO 03/049666 3 d | 7 d |
|---|---|---|---|---|---|
| Prior art (WO 03/049666) | | | 3.7 | n.a. | n.a. |
| Copolymer 6 | 12.1 | 5.5 | 5.1 | 1.6 | 1.4 |
| Copolymer 32 | 8.2 | 4.7 | 4.1 | 1.3 | 1.1 |
| Copolymer 33 | 5.1 | 4.2 | 3.9 | 1.2 | 1.1 |
| Copolymer 30 | 19.1 | 5.3 | 5.5 | 1.5 | 1.5 |
| Copolymer 35 | 5.1 | 6.3 | 6.2 | 1.8 | 1.7 |

The polyester sheets washed in the presence of the copolymers according to the invention smelled stronger than the monomeric Prior art (WO 03/049666).

The same test was performed with copolymer 37 (with a low $M_w$ of 4100 Da and releasing citral as an α,β-unsaturated aldehyde instead of δ-damascone). The tests were carried out on polyester sheets. The pure α,β-unsaturated aldehyde citral was also included as a reference, the results are reported in Table 18.

TABLE 18

| Tested molecule | Evaluation after 3 d on polyester | Evaluation after 7 d on polyester | Ratio Invention/Prior art WO 03/049666 3 d | 7 d |
|---|---|---|---|---|
| Citral | 2.7 | 2.4 | n.a. | n.a. |
| Copolymer 37 | 4.0 | 4.0 | 1.5 | 1.7 |

The polyester sheets washed in the presence of copolymer 37 according to the invention smelled much stronger than the reference α,β-unsaturated aldehyde (citral).

Example 10

Olfactive Evaluation of the Release of a Perfuming Ingredient (Ionone) from the Invention's Copolymers Prepared in the Presence (34) or Absence (39) Catalyst Incorporated into a Consumer Product (Liquid Detergent)

A washing machine (Miele Novotronic W300-33CH) was loaded with 10 small terry towels (18 cm×18 cm, about 30 g each), and 6 large cotton towels for a total wash load of 2 kg. The load was washed at 40° C. using a short cycle program and rinsed twice at 900 rpm.

At the end of the washing, the 10 small terry towels were line-dried for 24 h and wrapped into aluminum foil for storage, before being evaluated for their olfactive intensity by 20 panelists after 4 and 7 days, using a scale ranging from "1" (no odor) to "7" (very strong odor). The following average intensities were determined for the different samples (Table 19).

TABLE 19

| Tested molecule | Viscosity (Pa · s) | $M_w$ (Da) | Evaluation after 4 days on cotton | Evaluation after 7 days on cotton |
|---|---|---|---|---|
| Copolymer 34 | 6.2 | 3100[a] | 3.2 | 3.2 |
| Copolymer 39 | 8.4 | 6500[a] | 3.3 | 3.4 | n.a. = not applicable;
[a]weight average molecular weight.

There is no significant difference between the two copolymers.

The same test was performed using polyester instead of cotton sheets, the results are reported in Table 20 and are in line with the those determined on cotton.

TABLE 20

| Tested molecule | $M_w$ (Da) | Evaluation after 4 d on polyester | Evaluation after 7 d on polyester |
|---|---|---|---|
| Copolymer 34 | 3100[a] | 3.2 | 3.6 |
| Copolymer 39 | 6500[a] | 3.2 | 3.9 | n.a. = not applicable;
[a]weight average molecular weight.

Example 11

Olfactive Evaluation of the Release of a Perfuming Ingredient from the Invention's Copolymers Incorporated into a Consumer Product (Milky Shampoo)

The liberation of an α,β-unsaturated ketone from the present invention's copolymers of formula (I) was tested in a shampoo application on hair using a milky shampoo formulation with the following final composition:

| | |
|---|---|
| Deionized water | 40.8% by weight |
| Jaguar ® C-14S (origin: Rhodia) | 0.4% by weight |
| Dehyton ® AB-30 (origin: Cognis) | 7.0% by weight |
| Texapon ® NSO IS (origin: Cognis) | 45.2% by weight |
| Dow Corning ® 2-1691 Emulsion (origin: Dow Corning ®) | 3.0% by weight |
| Cutina ® AGS (origin: Cognis) | 0.9% by weight |
| Rewomid ® IPP 240 (origin: Degussa) | 1.2% by weight |
| Cetyl alcohol | 1.2% by weight |
| Glydant ® Plus Liquid (origin: Lonza) | 0.3% by weight |

An α,β-unsaturated ketone, serving as the reference, (δ-damascone, 0.050% by weight, or damascenone, 0.025% by weight) was added to the above described milky shampoo formulation. Then the corresponding copolymer (6—releasing δ-damascone, 0.088% by weight, or 32—releasing damascenone, 0.044% by weight) of the invention, prepared in Example 1, was dispersed in an additional sample of the above described milky shampoo formulation, to release an equimolar amount of the corresponding α,β-unsaturated ketone as the reference sample. Similarly, a further reference sample containing an equimolar amount of Prior art (WO 03/049666, 0.1% by weight) was prepared and evaluated under the same conditions.

The samples were left macerating at room temperature for at least 24 h. Then hair swatches (10.0 g) were wetted during 30 s with hand warm tap water (at about 37° C.). Each hair swatch was then washed with the milky shampoo formulation (2.5 g) with gentle rubbing between the fingers for 30 s, before being rinsed with hand warm tap water (at about 37° C.) for 30 s. The swatches were then washed again with the milky shampoo formulation (2.5 g) for 30 s and rinsed for 30 s with hand warm tap water. The hair swatches were then dried at room temperature and evaluated olfactively after 6 h, 24 h, 48 h or 72 h. For the evaluation, the panelists rated the perceived odor intensity on a scale ranging from "1" (imperceptible), "2" (slightly perceptible), "3" (weak), "4" (medium), "5" (sustained), "6" (intense) to "7" (very intense). The data obtained from the panel evaluation are summarized in Table 21.

TABLE 21

| Tested molecule | Evaluation after 6 h | Evaluation after 24 h | Evaluation after 48 h | Evaluation after 72 h |
|---|---|---|---|---|
| δ-Damascone (reference) | n.m. | 1.8 | 1.5 | 1.1 |
| Prior art (WO 03/049666) | n.m. | 1.3 | 1.4 | 2.2 |
| Copolymer 6 | n.m. | 1.9 | 2.8 | 2.4 |
| Damascenone (reference) | 1.7 | 1.6 | 1.5 | n.m. |
| Copolymer 32 | 2.8 | 3.5 | 3.3 | n.m. | n.m. = not measured.

The results show that both copolymers according to the invention perform as good or even better than their corresponding reference α,β-unsaturated ketone in a shampoo application. In particular, after more than one day both copolymers perform much better than an equimolar amount of their corresponding reference α,β-unsaturated ketone. Copolymer 6 also performed better than the Prior art (WO 03/049666) monomer.

Example 12

Olfactive Evaluation of the Release of a Perfuming Ingredient from the Invention's Copolymers Incorporated into a Consumer Product (Rinse-Off Hair Conditioner)

The liberation of an α,β-unsaturated ketone from the present invention's copolymers of formula (I) was tested in a rinse-off conditioner on hair using a rinse-off conditioner formulation with the following final composition:

| | |
|---|---|
| Deionized water | 92.54% by weight |
| Chlorhexidine dihydrochloride | 0.05% by weight |
| Natrosol ® 250 H (origin: Hercules) | 1.00% by weight |
| Dehyquart ® C 4046 (origin: Cognis) | 0.20% by weight |
| Mirasil ® ADM-E (origin: Rhodia) | 1.20% by weight |
| Genamin ® KDM (origin: Clariant) | 1.00% by weight |
| Crodamol ® SS (origin: Croda) | 0.50% by weight |
| Crodacol ® C90 (origin: Croda) | 3.01% by weight |
| Myrisityl alcohol (origin: Aldrich) | 0.20% by weight |
| Nipagin ® M (origin: Nipa) | 0.30% by weight |

An α,β-unsaturated ketone, serving as the reference, (δ-damascone, 0.050% by weight, or damascenone, 0.025% by weight) was added to the above described rinse-off conditioner formulation. Then the corresponding copolymer (6—releasing δ-damascone, 0.088% by weight, or 32—releasing damascenone, 0.044% by weight) of the invention, prepared in Example 1, was dispersed in an additional sample of the above described rinse-off conditioner formulation, to release an equimolar amount of the corresponding α,β-unsaturated ketone as the reference sample. Similarly, a further reference sample containing an equimolar amount of Prior art (WO 03/049666, 0.1% by weight) was prepared and evaluated under the same conditions.

The samples were left macerating at room temperature for at least 24 h. Then the hair swatches (10.0 g, dried in an oven at 46° C. for 24 h) were each rinsed during 30 s with hand warm tap water (at about 37° C.) while rubbing carefully. Excess water was squeezed out with the fingertips. Then an unperfumed milky shampoo base (2.5 g, prepared as described in Example 11) was applied with a syringe (5 mL) along the hair swatch. The hair swatches were rubbed between fingertips to distribute the shampoo during 30 s until good lather develops, and then rinsed with tap water (at about 37° C.) for 30 s, while carefully rubbing. The excess water was squeezed out with the fingertips. The rinse-off conditioner (1.0 g) containing a copolymer according to the invention or the corresponding reference α,β-unsaturated ketone was applied with a syringe (1 mL). The sample was distributed on the hair with gentle rubbing between the fingertips during 1 min, then the hair swatches were combed, rinsed with tap water at about 37° C. during 30 s, while carefully rubbing. The excess water was squeezed out with the fingertips. The hair swatches were dried at room temperature and evaluated olfactively after 6 h and/or 24 h. For the evaluation, the panelists rated the perceived odor intensity on a scale ranging from "1" (imperceptible), "2" (slightly perceptible), "3" (weak), "4" (medium), "5" (sustained), "6" (intense) to "7" (very intense). The data obtained from the panel evaluation are summarized in Table 22.

TABLE 22

| Tested molecule | Evaluation after 6 h | Evaluation after 24 h |
|---|---|---|
| δ-Damascone (reference) | n.m. | 2.0 |
| Prior art (WO 03/049666) | n.m. | 2.0 |
| Copolymer 6 | n.m. | 2.6 |
| Damascenone (reference) | 2.6 | 2.3 |
| Copolymer 32 | 3.8 | 3.1 | n.m. = not measured.

The results show that the copolymers according to the invention are suitable for rinse-off hair conditioning applications. They perform better than the corresponding reference α,β-unsaturated ketone and, in the case of δ-damascone as the reference, also better than the Prior art (WO 03/049666) monomer.

Example 13

Olfactive Evaluation of the Release of a Perfuming Ingredient from the Invention's Copolymers Incorporated into a Consumer Product (All-Purpose Surface Cleaner)

The liberation of an α,β-unsaturated ketone from the present invention's copolymers of formula (I) was tested in an all-purpose surface cleaner (APC). An APC formulation with the following final composition has been prepared:

| Neodol ® 91-8 (origin: Shell Chemicals) | 5.0% by weight |
| Marlon ® A 375 (origin: Huls AG) | 4.0% by weight |
| Sodium cumolsulphonate | 2.0% by weight |
| Kathon ® CG (origin: Rohm and Haas) | 0.2% by weight |
| Water | 88.8% by weight |

One of the invention's copolymers of formula (I) was weighed into the above described APC formulation (0.8 mL) and THF (0.2 mL) at a concentration to release a total amount of 0.012 mmol of an α,β-unsaturated ketone (δ-damascone). Then the sample was diluted with demineralized tap water (9 mL). Another sample containing an equimolar amount of the unmodified α,β-unsaturated ketone to be released instead of the invention's copolymer of formula (I) was prepared in the same way as the reference. The samples were shaken and then deposited as a film onto a porous ceramic plate (ca. 5×10 cm) by carefully pipetting 0.75 mL of the diluted samples onto the surface of the substrate. The samples were then covered with a crystallizing dish (ca. 2.5 L) and left standing at room temperature. After one day, the substrates were placed inside a headspace sampling cell (ca. 625 mL) and exposed to a constant air flow of ca. 200 mL/min. The air was filtered through active charcoal and aspirated through a saturated solution of NaCl (to ensure a constant humidity of the air of ca. 75%). During 135 min the headspace system was left equilibrating, and then the volatiles were adsorbed during 15 minutes on a clean Tenax® cartridge. The cartridges were desorbed and analyzed as described in Example 2. All measurements were performed at least twice.

The headspace concentrations measured after 150 min of sampling above the porous ceramic plate are listed in Table 23 and compared to the headspace concentrations of the corresponding unmodified α,β-unsaturated ketone to be released from the compounds of formula (I) used as the reference.

TABLE 23

Average headspace concentrations of α,β-unsaturated ketones released from the compounds of formula (I) as prepared in Example 1 and of the corresponding unmodified α,β-unsaturated ketone in an all purpose cleaner application after 1 day and sampling for 150 min.

| Compound from | Amount of α,β-unsaturated ketone (δ-damascone) released [ng/L] | Amount of unmodified α,β-unsaturated ketone (δ-damascone, reference) [ng/L] | Factor of increase with respect to the reference |
|---|---|---|---|
| Copolymer 15 | 14.5 | 7.0 | 2.1 |
| Copolymer 16 | 22.4 | 7.0 | 3.2 |
| Copolymer 17 | 30.4 | 7.0 | 4.3 |
| Copolymer 18 | 11.7 | 7.0 | 1.7 |
| Copolymer 19 | 18.8 | 7.0 | 2.7 |
| Copolymer 22 | 22.5 | 7.0 | 3.2 |
| Copolymer 23 | 19.8 | 7.0 | 2.8 |
| Copolymer 27 | 28.6 | 7.0 | 4.1 |
| Copolymer 28 | 32.8 | 7.0 | 4.7 |
| Copolymer 29 | 31.2 | 7.0 | 4.5 |

The data show that the polymers of formula (I) as prepared in Example 1 release considerably more α,β-unsaturated ketone in an APC application after 1 day than the unmodified reference α,β-unsaturated ketone.

What is claimed is:

1. A polymer, capable of releasing in a controlled manner an odoriferous α,β-unsaturated ketone or aldehyde, and comprising at least one repeating unit of formula

(I)

wherein the double hatched lines indicate the bonding to another repeating unit and $R^1$ represents a $C_1$ to $C_{16}$ hydrocarbon group;

P represents a group susceptible of generating an odoriferous α,β-unsaturated ketone or aldehyde and is represented by formula

(II)

in which the wavy line indicates the location of the bond between said P and X;

$R^2$ represents a hydrogen atom, a $C_1$ to $C_{15}$ linear, cyclic or branched alkyl, alkenyl or alkadienyl radical, optionally substituted by one to four $C_1$ to $C_4$ alkyl groups; and $R^3$, $R^4$ and $R^5$, independently of each other, represent a hydrogen atom, a $C_6$ to $C_{10}$ aromatic ring or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bound together to form a saturated or unsaturated ring having 5 to 20 carbon atoms and, including the carbon atom to which said $R^2$, $R^3$, $R^4$ or $R^5$ groups are bound, this ring being optionally substituted by one or two $C_1$ to $C_8$ linear, branched or cyclic alkyl or alkenyl groups;

X represents a sulfur atom; and

G represents a $C_2$-$C_5$ hydrocarbon group optionally comprising 1 or 2 oxygen, sulfur and/or nitrogen atoms.

2. A polymer according to claim 1, characterized in that P represents a group of the formulae (P-1) to (P-13), in the form of any one of its isomers:

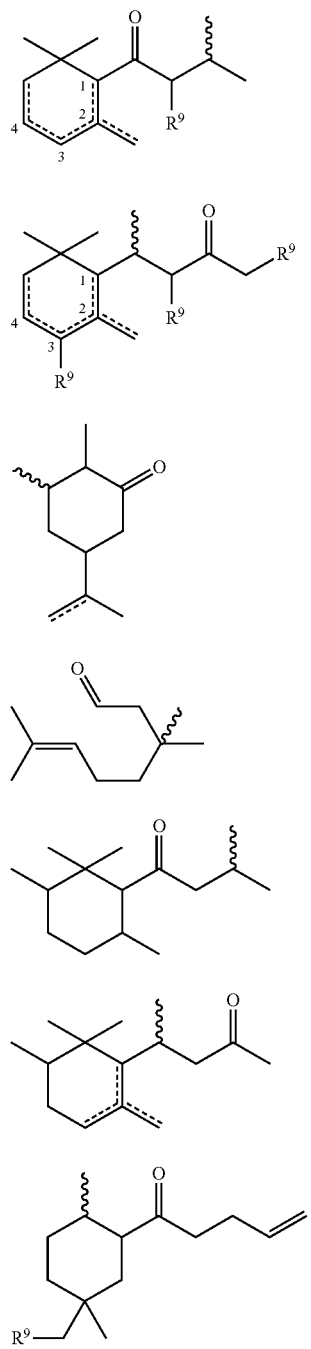

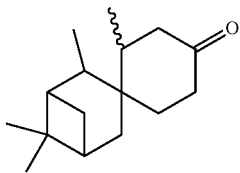

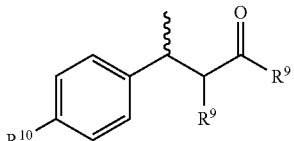

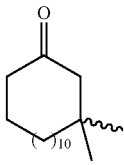

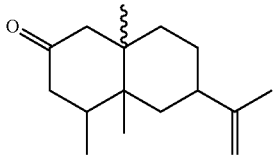

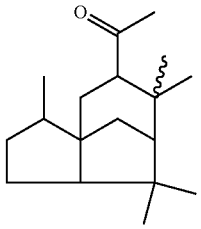

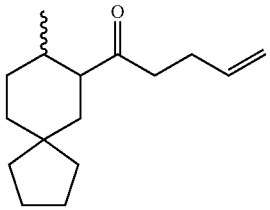

in which formulae the wavy lines have the meaning indicated in claim 1 and the dotted lines represent a single or double bond, $R^9$ being a hydrogen atom or a methyl group and $R^{10}$ representing a hydrogen atom, a hydroxy or methoxy group or a $C_1$-$C_4$ linear or branched alkyl group.

3. A method to confer, enhance, improve or modify the odor properties of a perfuming composition or of a perfumed article, which method comprises adding to said composition or article an effective amount of at least one polymer according to claim 2.

4. A polymer according to claim 1, wherein $R^1$ represents a methyl group.

5. A polymer according to claim 1, wherein polymer is characterized by a viscosity comprised in the range between 0.5 (Pa·s) and 60 (Pa·s).

6. A perfuming composition comprising:
i) as perfuming ingredient, at least one polymer according to claim 1;

ii) at least one ingredient selected from the group consisting of a perfumery carrier and a perfumery base; and iii) optionally at least one perfumery adjuvant.

7. A perfuming consumer product comprising as perfuming ingredient, at least one polymer according to claim 1.

8. A perfuming consumer product according to claim 7, in the form of a perfume, a fabric care product, a body-care product, an air care product or a home care product.

9. A perfuming consumer product according to claim 7, in the form of a rinse-off product.

10. A method to confer, enhance, improve or modify the odor properties of a perfuming composition or of a perfumed article, which method comprises adding to said composition or article an effective amount of at least one polymer according to claim 1.

11. A polymer, capable of releasing in a controlled manner an odoriferous α,β-unsaturated ketone or aldehyde, and comprising at least one repeating unit of formula

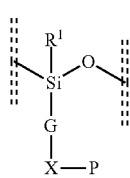

(I)

wherein the double hatched lines indicate the bonding to another repeating unit and $R^1$ represents a $C_1$ to $C_{16}$ hydrocarbon group;

P represents a group susceptible of generating an odoriferous α,β-unsaturated ketone or aldehyde and is represented by formula

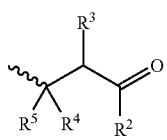

(II)

in which the wavy line indicates the location of the bond between said P and X;

$R^2$ represents a hydrogen atom, a $C_1$ to $C_{15}$ linear, cyclic or branched alkyl, alkenyl or alkadienyl radical, optionally substituted by one to four $C_1$ to $C_4$ alkyl groups; and $R^3$, $R^4$ and $R^5$, independently of each other, represent a hydrogen atom, a $C_6$ to $C_{10}$ aromatic ring or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bound together to form a saturated or unsaturated ring having 5 to 20 carbon atoms and, including the carbon atom to which said $R^2$, $R^3$, $R^4$ or $R^5$ groups are bound, this ring being optionally substituted by one or two $C_1$ to $C_8$ linear, branched or cyclic alkyl or alkenyl groups;

X represents a sulfur atom; and

G represents a $C_2$-$C_8$ hydrocarbon group optionally comprising 1 or 2 oxygen, sulfur and/or nitrogen atoms; and repeating units of the formulae (III) or (IV)

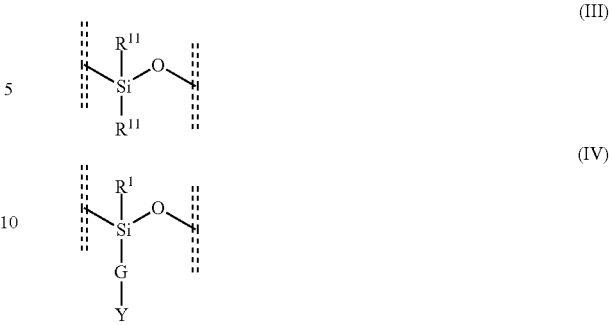

wherein the double hatched lines, G and $R^1$ have the same meaning as in any one of claims 1 to 2; each $R^{11}$ group represents independently of each other a $C_6$ to $C_{12}$ aromatic ring or a $C_1$ to $C_{18}$ linear, cyclic or branched alkyl group, or a $C_1$ to $C_6$ linear, cyclic or branched alkyloxy group; and Y represents a group of formulae a) to g)

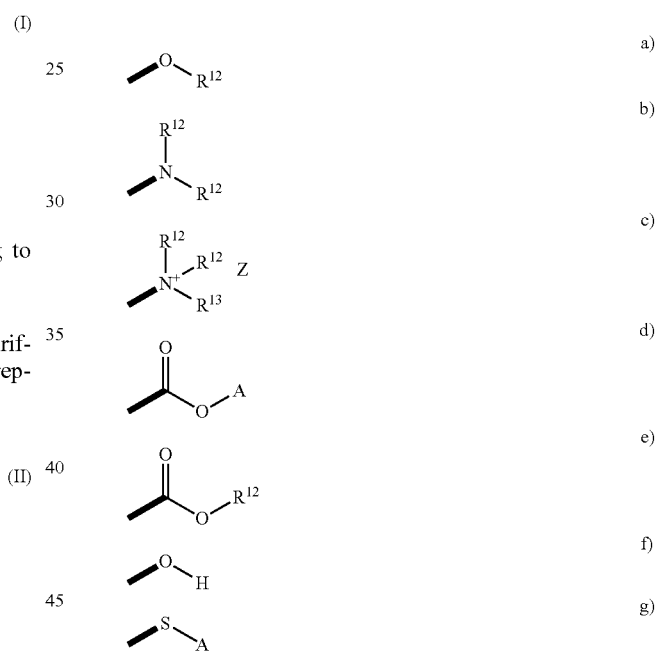

with A being a hydrogen atom or an alkali metal atom, $R^{12}$ being a $C_1$ to $C_{18}$ linear or branched alkyl group, $R^{13}$ being a hydrogen atom or a $R^{12}$ group and Z being a monoanion.

12. A polymer according to claim 11, wherein each $R^{11}$ is a methyl group.

13. A polymer according to claim 11, wherein Y represents a group of formula d), f) or g).

14. A polymer according to claim 11, wherein polymer is linear and comprises only:

siloxane units of formula (III) and/or (IV); and/or
siloxane units of formula (V)

—O—Si(OR$^{13}$)$_a$(G-B)$_b$(R$^{14}$)$_c$    (V)

wherein each a, b and c is either 0, 1, 2 or 3 and (a+b+c)=3;

G represents a group as defined in claim 1 or 2;

each B represents independently from each other a X-P group, as defined in claim 1 or 2, or a Y group;

each $R^{13}$ represents independently from each other a hydrogen atom or a $R^{12}$ group; and each $R^{14}$ represents independently from each other a $R^1$ or a $R^{11}$ group as defined in claims 1 to 2; and siloxane units of formula (I), as defined in any one of claims 1 to 2.

15. A polymer according to claim 11, wherein polymer is a linear co-polymer wherein the molar ratio of the repeating units (I)/[(III)+(IV)] is between 85/15 and 45/55;

X represents a sulfur atom;

$R^1$ is a methyl group;

G represents a linear $C_3$-$C_5$ alkanediyl group; and said polymer having a weight average molecular weight comprised in the range between 1000 Da and 5000 Da;

terminal groups of formula:

$$—O—Si(OR^{13})_a(R^{14})_c \quad (V')$$

wherein each a and c is either 0, 1, 2 or 3 and (a+c)=3;

each $R^{13}$ represents independently from each other a hydrogen atom or a $R^{12}$ group as defined above; and each $R^{14}$ represents independently from each other a $R^1$ or a $R^{11}$ group as defined above; and optionally a viscosity comprised in the range between 1.0 (Pa·s) and 60 (Pa·s).

16. A method to confer, enhance, improve or modify the odor properties of a perfuming composition or of a perfumed article, which method comprises adding to said composition or article an effective amount of at least one polymer according to claim 15.

17. A polymer according to claim 11, wherein G represents a $C_2$-$C_5$ hydrocarbon group.

18. A method to confer, enhance, improve or modify the odor properties of a perfuming composition or of a perfumed article, which method comprises adding to said composition or article an effective amount of at least one polymer according to claim 11.

19. A polymer, capable of releasing in a controlled manner an odoriferous α,β-unsaturated ketone or aldehyde, and comprising at least one repeating unit of formula

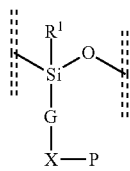

(I)

wherein the double hatched lines indicate the bonding to another repeating unit and $R^1$ represents a $C_1$ to $C_{16}$ hydrocarbon group;

P represents a group susceptible of generating an odoriferous α,β-unsaturated ketone or aldehyde and is represented by formula

(II)

in which the wavy line indicates the location of the bond between said P and X;

$R^2$ represents a hydrogen atom, a $C_1$ to $C_{15}$ linear, cyclic or branched alkyl, alkenyl or alkadienyl radical, optionally substituted by one to four $C_1$ to $C_4$ alkyl groups; and $R^3$, $R^4$ and $R^5$, independently of each other, represent a hydrogen atom, a $C_6$ to $C_{10}$ aromatic ring or a $C_1$ to $C_{15}$ linear, cyclic or branched alkyl, alkenyl or alkadienyl radical, possibly substituted by $C_1$ to $C_4$ alkyl groups; or two, or three, of the groups $R^1$ to $R^4$ are bound together to form a saturated or unsaturated ring having 5 to 20 carbon atoms and, including the carbon atom to which said $R^2$, $R^3$, or $R^4$ groups are bound, this ring being optionally substituted by one or two $C_1$ to $C_8$ linear, branched or cyclic alkyl or alkenyl groups;

X represents a sulfur atom; and

G represents a $C_2$-$C_5$ hydrocarbon group optionally comprising 1 or 2 oxygen, sulfur and/or nitrogen atoms;

wherein the polymer has a weight average molecular weight of between 1500 Da and 6500 Da.

20. A method to confer, enhance, improve or modify the odor properties of a perfuming composition or of a perfumed article, which method comprises adding to said composition or article an effective amount of at least one polymer according to claim 19.

\* \* \* \* \*

UNITED STATES PATENT AND TRADEMARK OFFICE
CERTIFICATE OF CORRECTION

PATENT NO. : 9,765,282 B2  
APPLICATION NO. : 14/900157  
DATED : September 19, 2017  
INVENTOR(S) : Berthier et al.

Page 1 of 1

It is certified that error appears in the above-identified patent and that said Letters Patent is hereby corrected as shown below:

In the Claims

Column 48:
Line 65, before "1 or 2", delete "claim" and insert -- claims --.
Line 67, before "1 or 2", delete "claim" and insert -- claims --.

Column 50:
Line 30, after "$R^3$," delete "or"; and after "$R^4$" insert -- or $R^5$ --.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*